US010201331B2

(12) United States Patent
Fleming et al.

(10) Patent No.: US 10,201,331 B2
(45) Date of Patent: Feb. 12, 2019

(54) BIOPSY TISSUE SAMPLE TRANSPORT DEVICE AND METHOD OF USING THEREOF

(71) Applicant: LEICA BIOSYSTEMS NUSSLOCH GmbH, Nussloch (DE)

(72) Inventors: Jo Fleming, San Diego, CA (US); Charles E. Clemens, Encinitas, CA (US); David Berardelli, San Diego, CA (US)

(73) Assignee: Leica Biosystems Nussloch GmbH, Nuβloch (DE)

( * ) Notice: Subject to any disclaimer, the term of this patent is extended or adjusted under 35 U.S.C. 154(b) by 278 days.

(21) Appl. No.: 14/403,898

(22) PCT Filed: Jun. 24, 2013

(86) PCT No.: PCT/US2013/047281
§ 371 (c)(1),
(2) Date: Nov. 25, 2014

(87) PCT Pub. No.: WO2013/192606
PCT Pub. Date: Dec. 27, 2013

(65) Prior Publication Data
US 2015/0209017 A1   Jul. 30, 2015

Related U.S. Application Data

(60) Provisional application No. 61/663,295, filed on Jun. 22, 2012, provisional application No. 61/663,310, (Continued)

(51) Int. Cl.
*A61B 10/00* (2006.01)
*A01N 1/02* (2006.01)
(Continued)

(52) U.S. Cl.
CPC ........ *A61B 10/0096* (2013.01); *A01N 1/0273* (2013.01); *A61B 10/02* (2013.01);
(Continued)

(58) Field of Classification Search
CPC . A61B 10/00; A61B 10/02; A61B 2010/0208; A01N 1/0273; B65D 25/108
See application file for complete search history.

(56) References Cited

U.S. PATENT DOCUMENTS 4,735,794 A   4/1988 Parkinson
5,401,625 A   3/1995 Robinson
(Continued)

FOREIGN PATENT DOCUMENTS

CN   101835428 A   9/2010
CN   101896274 A   11/2010
(Continued)

OTHER PUBLICATIONS

International Search Report of PCT/US2013/047281 dated Oct. 16, 2013 [PCT/ISA/210].
(Continued)

*Primary Examiner* — Neil N Turk
(74) *Attorney, Agent, or Firm* — Sughrue Mion, PLLC

(57) ABSTRACT

A biopsy tissue sample transport device and method of using thereof including a tissue storage assembly having a sample container, having a holding structure to hold a tissue sample, the holding structure having a sample access opening formed in a sidewall; a housing that receives the tissue storage assembly, the housing comprising an assembly insertion opening through which the tissue storage assembly is inserted into the housing; a sealing member configured to engage and substantially seal the sample access opening of the holding structure of the sample container of the tissue
(Continued)

storage assembly; and a lid to engage and substantially seal the assembly insertion opening of the housing.

18 Claims, 21 Drawing Sheets

Related U.S. Application Data filed on Jun. 22, 2012, provisional application No. 61/663,326, filed on Jun. 22, 2012.

(51) Int. Cl.
| | |
|---|---|
| *A61B 10/02* | (2006.01) |
| *B65D 25/10* | (2006.01) |
| *B65D 25/20* | (2006.01) |
| *B65D 43/00* | (2006.01) |
| *B65D 51/28* | (2006.01) |
| *B65D 53/02* | (2006.01) |
| *G01N 1/00* | (2006.01) |
| *A61B 90/90* | (2016.01) |

(52) U.S. Cl.
CPC ............ *A61B 90/90* (2016.02); *B65D 25/108* (2013.01); *B65D 25/205* (2013.01); *B65D 43/00* (2013.01); *B65D 51/2842* (2013.01); *B65D 53/02* (2013.01); *G01N 1/00* (2013.01); *A61B 2010/0208* (2013.01)

(56) References Cited

U.S. PATENT DOCUMENTS

| | | | |
|---|---|---|---|
| 5,447,841 A | 9/1995 | Gray et al. | |
| 5,601,650 A | 2/1997 | Goldbecker et al. | |
| 5,695,942 A | 10/1997 | Farmilo et al. | |
| 5,817,032 A | 10/1998 | Williamson et al. | |
| 5,833,057 A | 11/1998 | Char et al. | |
| 5,895,628 A | 4/1999 | Heid et al. | |
| 5,965,454 A | 10/1999 | Farmilo et al. | |
| 5,968,436 A | 10/1999 | Takezaki | |
| 6,042,874 A | 3/2000 | Visinoni et al. | |
| 6,103,518 A | 8/2000 | Leighton | |
| 6,207,408 B1 | 3/2001 | Essenfeld et al. | |
| 6,270,464 B1 | 8/2001 | Fulton, III et al. | |
| 6,311,945 B1 | 11/2001 | DAngelo | |
| 6,329,645 B2 | 12/2001 | Giberson et al. | |
| 6,356,782 B1 | 3/2002 | Sirimanne et al. | |
| 6,372,512 B1 | 4/2002 | Kerschmann | |
| 6,383,801 B1 | 5/2002 | Leighton | |
| 6,444,170 B1 | 9/2002 | Heid et al. | |
| 6,465,245 B1 | 10/2002 | Walton et al. | |
| 6,468,783 B1 | 10/2002 | Leighton | |
| 6,513,803 B2 | 2/2003 | Morales et al. | |
| 6,521,186 B1 | 2/2003 | Izvoztchikov et al. | |
| 6,586,713 B2 | 7/2003 | Essenfeld et al. | |
| 6,596,479 B1 | 7/2003 | Gray et al. | |
| 6,699,205 B2 | 3/2004 | Fulton, III et al. | |
| 6,793,890 B2 | 9/2004 | Morales et al. | |
| 6,797,928 B2 | 9/2004 | Giberson et al. | |
| 6,803,018 B1 | 10/2004 | Stiller | |
| 6,875,583 B2 | 4/2005 | Giberson et al. | |
| 6,902,928 B2 | 6/2005 | Izvoztchikov et al. | |
| 6,991,934 B2 | 1/2006 | Walton et al. | |
| 7,005,110 B2 | 2/2006 | Taft et al. | |
| 7,075,045 B2 | 7/2006 | Visinoni | |
| 7,147,826 B2* | 12/2006 | Haywood ............... B01L 3/502 215/306 |
| 7,155,050 B1 | 12/2006 | Sloge et al. | |
| 7,156,814 B1 | 1/2007 | Williamson, IV et al. | |
| 7,179,424 B2 | 2/2007 | Williamson, IV et al. | |
| 7,217,392 B2 | 5/2007 | Bogen et al. | |
| 7,219,884 B2 | 5/2007 | Morales | |
| 7,229,417 B2 | 6/2007 | Foerster et al. | |
| 7,273,587 B1 | 9/2007 | Birkner et al. | |
| 7,273,720 B1 | 9/2007 | Birkner et al. | |
| 7,329,533 B2 | 2/2008 | Fredenburgh | |
| 7,470,401 B2 | 12/2008 | Morales | |
| 7,521,021 B2 | 4/2009 | McCormick | |
| 7,526,987 B2 | 5/2009 | Morales | |
| 7,544,953 B2 | 6/2009 | Goodman | |
| 7,547,538 B2 | 6/2009 | Morales et al. | |
| 7,553,672 B2 | 6/2009 | Bogen et al. | |
| 7,572,236 B2 | 8/2009 | Quick et al. | |
| 7,575,556 B2 | 8/2009 | Speeg et al. | |
| 7,576,307 B2 | 8/2009 | Yazdanfar et al. | |
| 7,584,019 B2 | 9/2009 | Feingold et al. | |
| 7,593,787 B2 | 9/2009 | Feingold et al. | |
| 7,603,201 B2 | 10/2009 | Feingold et al. | |
| 7,618,828 B2 | 11/2009 | Bleuel et al. | |
| 7,625,397 B2 | 12/2009 | Foerster et al. | |
| 7,657,070 B2 | 2/2010 | Lefebvre | |
| 7,663,101 B2 | 2/2010 | Goodman | |
| 7,666,620 B2 | 2/2010 | Wiederhold | |
| 7,687,255 B2 | 3/2010 | Chu | |
| 7,722,810 B2 | 5/2010 | Allen et al. | |
| 7,767,434 B2 | 8/2010 | Chu | |
| 7,776,274 B2 | 8/2010 | Williamson, IV et al. | |
| 7,780,919 B2 | 12/2010 | McCormick | |
| 7,850,912 B2 | 12/2010 | Favuzzi et al. | |
| 7,854,707 B2* | 12/2010 | Hibner ............... A61B 10/0096 600/567 |
| 7,881,517 B2 | 2/2011 | Sloge et al. | |
| 7,888,132 B2 | 2/2011 | McCormick | |
| 7,901,634 B2 | 3/2011 | Testa et al. | |
| 7,914,462 B2 | 3/2011 | Hutchins et al. | |
| 7,914,738 B2 | 3/2011 | Hutchins et al. | |
| 8,118,775 B2 | 2/2012 | Grunewald et al. | |
| 2005/0084425 A1 | 4/2005 | Williamson, IV et al. | |
| 2005/0112032 A1 | 5/2005 | McCormick | |
| 2005/0142631 A1 | 6/2005 | Mosconi et al. | |
| 2005/0147538 A1 | 7/2005 | Williamson, IV et al. | |
| 2006/0147896 A1 | 7/2006 | Schnetz et al. | |
| 2006/0177812 A1 | 8/2006 | Schnetz et al. | |
| 2006/0228772 A1 | 10/2006 | Donndelinger | |
| 2007/0072167 A1 | 3/2007 | Rochaix | |
| 2007/0104618 A1 | 5/2007 | Williamson, IV et al. | |
| 2007/0116612 A1 | 5/2007 | Williamson, IV | |
| 2007/0141711 A1 | 6/2007 | Stephens et al. | |
| 2007/0161609 A1 | 7/2007 | Buck et al. | |
| 2007/0166834 A1 | 7/2007 | Williamson, IV et al. | |
| 2007/0218542 A1 | 9/2007 | Li et al. | |
| 2008/0026366 A1 | 1/2008 | Harkins | |
| 2008/0138854 A1 | 6/2008 | Williamson | |
| 2008/0193014 A1 | 8/2008 | Ecker et al. | |
| 2008/0206807 A1 | 8/2008 | Duymelinck et al. | |
| 2008/0214955 A1 | 9/2008 | Speeg et al. | |
| 2008/0220468 A1 | 9/2008 | Windeyer et al. | |
| 2008/0227144 A1 | 9/2008 | Nightingale | |
| 2008/0254504 A1 | 10/2008 | Vom et al. | |
| 2008/0268496 A1 | 10/2008 | Mosconi et al. | |
| 2008/0274496 A1 | 11/2008 | Duymelinck et al. | |
| 2009/0098522 A1 | 4/2009 | Marcovitz | |
| 2009/0104692 A1 | 4/2009 | Bartfeld et al. | |
| 2009/0145920 A1 | 6/2009 | Kerrod et al. | |
| 2009/0165940 A1 | 7/2009 | Baur et al. | |
| 2009/0170152 A1 | 7/2009 | Reeser et al. | |
| 2009/0183581 A1* | 7/2009 | Wilkinson ............... B01L 3/502 73/864.91 |
| 2009/0191544 A1 | 7/2009 | Dela Torre Bueno | |
| 2009/0203066 A1 | 8/2009 | Perrut et al. | |
| 2009/0208105 A1 | 8/2009 | Bystrov et al. | |
| 2009/0222746 A1 | 9/2009 | Chirica et al. | |
| 2009/0253199 A1 | 10/2009 | McCormick | |
| 2010/0017030 A1 | 1/2010 | Feingold et al. | |
| 2010/0005563 A1 | 3/2010 | Konrad et al. | |
| 2010/0061632 A1 | 3/2010 | Young et al. | |
| 2010/0075410 A1 | 3/2010 | Desai et al. | |
| 2010/0092064 A1 | 4/2010 | Li | |
| 2010/0093023 A1 | 4/2010 | Gustafsson et al. | |
| 2010/0099140 A1 | 4/2010 | Donndelinger | |
| 2010/0112624 A1 | 5/2010 | Metzner et al. | |
| 2010/0112625 A1 | 5/2010 | Erben et al. | |
| 2010/0144002 A1 | 6/2010 | Donndelinger | |

(56) References Cited

U.S. PATENT DOCUMENTS

| | | |
|---|---|---|
| 2010/0167334 A1 | 7/2010 | Williamson, IV |
| 2010/0167338 A1 | 7/2010 | Amano et al. |
| 2010/0182877 A1 | 7/2010 | Chu |
| 2010/0184127 A1 | 7/2010 | Williamson, IV et al. |
| 2010/0208955 A1 | 8/2010 | Mehes et al. |
| 2010/0223935 A1 | 9/2010 | Donndelinger |
| 2010/0248301 A1 | 9/2010 | Ulbrich et al. |
| 2010/0278627 A1 | 11/2010 | Williamson, IV et al. |
| 2010/0279341 A1 | 11/2010 | Steiner et al. |
| 2010/0323395 A1 | 12/2010 | Ulbrich et al. |
| 2010/0330660 A1 | 12/2010 | Hutchins et al. |
| 2011/0008884 A1 | 1/2011 | Morales |
| 2011/0034341 A1 | 2/2011 | Mehes et al. |
| 2011/0045565 A1 | 2/2011 | Sanders et al. |
| 2011/0054679 A1 | 3/2011 | Lefebvre et al. |
| 2011/0060766 A1 | 3/2011 | Ehlke et al. |
| 2011/0076753 A1 | 3/2011 | Goerner et al. |

FOREIGN PATENT DOCUMENTS

| | | |
|---|---|---|
| DE | 102007011329 A1 | 9/2008 |
| DE | 102008005265 A1 | 7/2009 |
| DE | 102009010667 A1 | 9/2010 |
| EP | 0807807 A1 | 11/1997 |
| EP | 1508026 | 2/2005 |
| EP | 1545775 | 6/2005 |
| EP | 1682272 | 7/2006 |
| EP | 1782737 A1 | 5/2007 |
| EP | 1975595 A1 | 10/2008 |
| EP | 1985383 A1 | 10/2008 |
| EP | 2002894 A1 | 12/2008 |
| EP | 2091440 | 8/2009 |
| JP | 2011501198 A | 1/2011 |
| JP | 2011502254 A | 1/2011 |
| WO | 0019897 A1 | 4/2000 |
| WO | 2004/028693 A1 | 4/2004 |
| WO | 2005/037182 A2 | 4/2005 |
| WO | 2008/073387 A1 | 6/2008 |
| WO | 2009/055605 A2 | 4/2009 |
| WO | 2009055603 A2 | 4/2009 |
| WO | 2009055605 A1 | 4/2009 |
| WO | 2010/030358 A1 | 3/2010 |
| WO | 2010/085626 A1 | 7/2010 |
| WO | 2010/112316 A1 | 10/2010 |
| WO | 2011041495 A1 | 4/2011 |
| WO | 2011/133453 A2 | 10/2011 |
| WO | 2013192606 A1 | 12/2013 |

OTHER PUBLICATIONS

Written Opinion of PCT/US2013/047281 dated Oct. 16, 2013 [PCT/ISA/237].

Communication dated Jun. 21, 2016, from the State Intellectual Property Office of the People's Republic of China in counterpart application No. 201380032750.0.

Communication dated Jan. 26, 2016, issued by the European Patent Office in corresponding European Application No. 13806129.6.

Japanese Office Action; Application No. 2015-518634; dated Jan. 19, 2017.

Communication dated Jan. 24, 2017, from the Japanese Patent Office in counterpart application No. 2015-518634.

Communication dated Oct. 14, 2015 from the State Intellectual Property Office of the People's Republic of China in counterpart application No. 201380032750.0.

* cited by examiner

BIOPSY TISSUE SAMPLE TRANSPORT DEVICE AND METHOD OF USING THEREOF

REFERENCE TO RELATED APPLICATION

Reference is hereby made to U.S. Provisional Patent Application Ser. No. 61/663,295, filed Jun. 22, 2012 and entitled BIOPSY TISSUE SAMPLE TRANSPORT DEVICE; U.S. Provisional Patent Application Ser. No. 61/663,310, filed Jun. 22, 2012 and entitled BIOPSY TISSUE SAMPLE TRANSPORT DEVICE AND METHODS; and U.S. Provisional Patent Application Ser. No. 61/663, 326, filed Jun. 22, 2012 and entitled BIOPSY TISSUE SAMPLE TRANSPORT DEVICE, the disclosures of which is hereby incorporated by reference and priority of which is hereby claimed pursuant to 37 CFR 1.78(a)(4) and (5)(i).

FIELD OF THE INVENTION

The present disclosure relates generally to tissue sample transport devices, and in particular, to a tissue sample transport device configured to transport a biopsy core sample.

BACKGROUND

A biopsy is the removal of tissue to examine it for signs of cancer or other disorders. Biopsies may be open (surgically removing tissue) or percutaneous (e.g. by fine needle aspiration, core needle biopsy or vacuum assisted biopsy). The biopsy site can be located via palpation, ultrasound, stereotactic, MRI or mammography.

Biopsy samples are obtained in a variety of ways using various medical procedures involving a variety of the sample collection devices. Examples of collection devices include those marketed under the tradenames MAMMOTOME (from DEVICOR MEDICAL PRODUCTS, Cincinnati Ohio), CELERO, ATEC AND EVIVA (all from HOLOGIC, Malborough Mass.), and FINESSE and ENCOR (all from BARD BIOPSY SYSTEMS, Tempe Ariz.).

Some of these systems collect the biopsy sample in a closed container. U.S. Pat. No. 8,118,775 describes a closed biopsy sample storage container that is designed to spatially segregate biopsy samples during the collection procedure. U.S. Pat. No. 7,572,236 describes a biopsy device with a closed container for collecting one or more samples. The container includes a basket for flushing away blood and other tissue debris from the specimens.

After the biopsy sample is collected, the sample is analyzed at a lab that is set up to perform the appropriate tests (such as histological analysis). Often, collection of the sample, and analysis of the sample are performed at different locations and the sample must be transported from the collection location (e.g. hospital, clinic, etc.) to the pathology lab for analysis.

Thus, after collection, the biopsy samples are typically removed from the collection container and placed into another container for transport to a pathology lab. A chemical fixative (such as formalin) is added to the container to preserve the sample.

After the samples are removed from the patient, a tissue marker can be inserted into the biopsy site to later relocate the site, if needed. For example, U.S. Pat. Nos. 6,270,464, 6,356,782, 6,699,205, 7,229,417 and 7,625,397 all describes tissue markers and methods for marking a biopsy site.

It is desirable to retain information collected during the biopsy with each sample. It is also desirable to be able to later relocate the position that the sample was taken from the biopsy site by correlating information retained with the sample against the tissue marker.

Thus, there is a need for the sample or samples to be packaged for transportation from the collection location to the pathology lab. Currently, the sample is simply placed loosely in a specimen jar filled with the fixing agent or chemical (e.g., a solution of formaldehyde in water such as Formalin), which preserves the biopsy sample for analysis and the specimen jar sealed for shipping. If multiple samples are collected, multiple samples from the same patient may be placed in the same jar for transportation.

Once the biopsy sample arrives in the pathology lab, it is removed from the container placed, into a cassette and processed it is then embedded ready for sectioning. It is often necessary to slice the sample into a plurality of thin sections (e.g., 2 to 25µ thick sections), often using a microtome, prior to performing any analysis. Such sectioning of the sample often helps a medical professional properly assess the sample under a microscope (e.g. diagnose relationships between cells and other constituents of the sample, or perform other assessments). In order to properly section the sample, several steps are typically performed to embed the sample within a solid substrate. A commonly used solid substrate may include, for example, paraffin wax, which is used to hold the sample in position while also providing a uniform consistency to further facilitate sectioning with the microtome. In order to properly process the sample a series of steps must be performed including:

1—Fixation of the sample to immobilize molecular components and/or prevent degradation. This is typically done with a fixing agent or chemical (e.g., a solution of formaldehyde in water such as formalin) shortly after sample collection.

2—Transferring the sample from the transportation jar to a processing cassette.

3—Infiltrating the sample with an embedding material, such as the paraffin wax.

4—Embedding the sample in the paraffin wax and sectioning using for example a microtome.

Under existing practices, this fixing, transferring, infiltrating, and embedding must all be done manually, and such manual handling of the sample can increase the likelihood of misidentifying the sample, cross contaminating the samples, or losing part or all of the sample. Further, as multiple samples may be placed in the same jar, and each sample is merely loosely floating in the fixing agent, information about each sample, such as the orientation of the sample with respect to collection and, which sample was collected from which area of the patient (i.e., 2 mm from mass, 4 mm from mass, 6 mm from mass etc.) may be lost and unavailable to the medical professional when assessing the sample. Additionally, the numerous steps of manual manipulation can often increase the time that it takes to provide a proper assessment for each sample, once the sample is collected from the patient.

SUMMARY

In view of these issues, there may be a need for a transportation device that can transport one or more samples while still preserving information regarding the collection such as patient name and details, the orientation of the sample with respect to the sample collection site, the number of samples collected and location from which the sample was collected on the patient during transport between the collection site (e.g. hospital, clinic, etc.) and the pathology lab performing the analysis. Further, other information regarding collection conditions such as time between collection of sample and placement in the fixing agent, and pH of the fixing agent may also be preserved. Additionally, there may be a need for a transportation device that may reduce the amount of manual manipulation required between sample collection and assessment by a medical professional.

Thus, example embodiments of this application may address one or more of the above identified issues. However, an embodiment of this application need not solve, address, or otherwise improve on existing technologies.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are reused to indicate correspondence between referenced elements.

DETAILED DESCRIPTION

In the following detailed description, reference will be made to the accompanying drawing(s), in which similar elements are designated with similar numerals. The aforementioned accompanying drawings show by way of illustration and not by way of limitation, specific example embodiments and implementations consistent with principles of an example embodiment. These implementations are described in sufficient detail to enable those skilled in the art to practice an example embodiment and it is to be understood that other implementations may be utilized and that structural changes and/or substitutions of various elements may be made without departing from the scope and spirit of an example embodiment. The following detailed description is, therefore, not to be construed in a limited sense.

Embodiment 1

Figure 1:
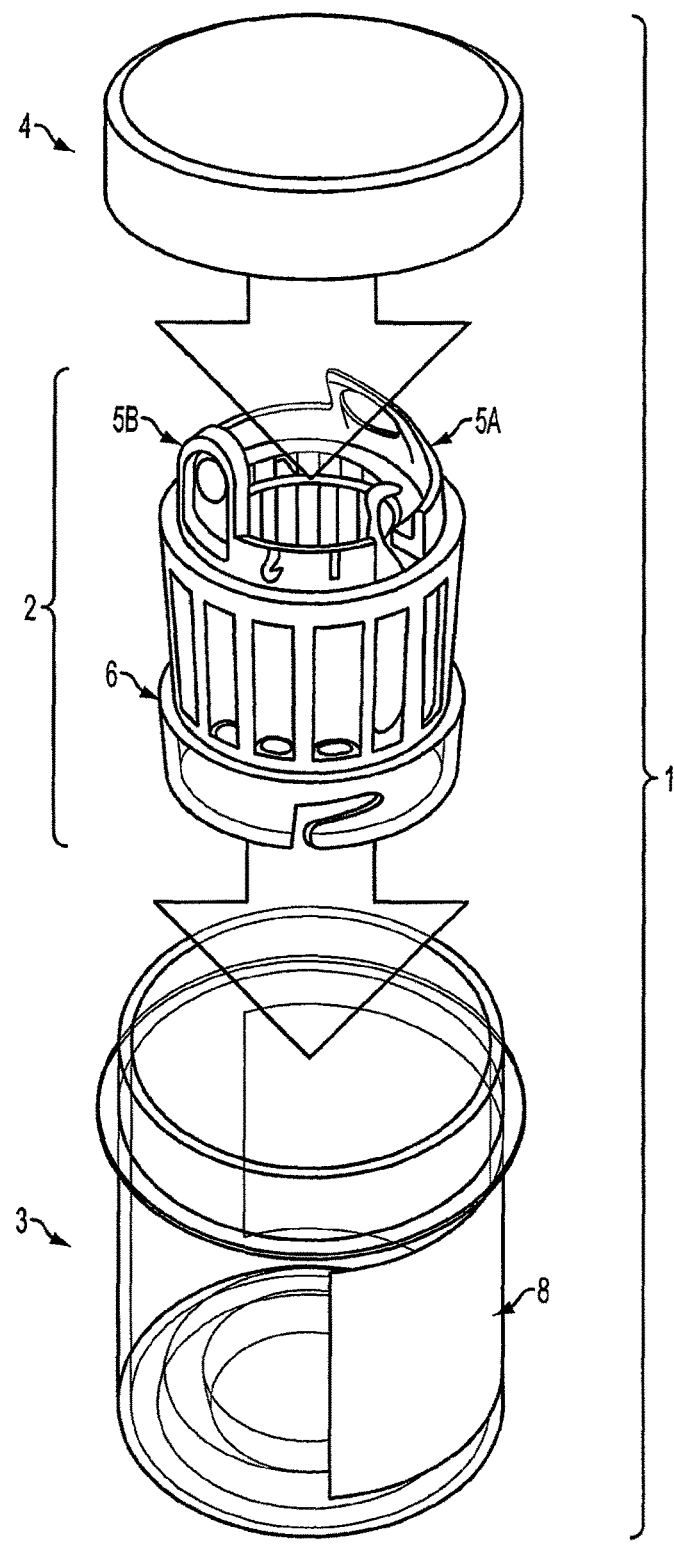
FIG. 1 illustrates an exploded view of a biopsy tissue sample transport device according to a first embodiment of the present application.

FIG. 1 illustrates an exploded view of a biopsy tissue sample transport device 1 according to a first embodiment of the present application. The biopsy tissue sample transport device 1 of this example comprises a tissue storage assembly 2, a housing 3, and a lid 4. The tissue storage assembly 2 comprises at least one sample tray (in this embodiment two trays are shown as 5A, 5B) and a bracing member 6. The tissue storage assembly 2, the sample trays 5A, 5B, and the bracing member 6 are discussed in more detail below. In some embodiments, the housing 3 may have a label 8 attached to housing 3.

In one embodiment, the tissue storage assembly 2 is sized and shaped to fit a Mammotome system. In one embodiment, the tissue storage assembly 2 is as described in FIGS. 10-16 and the corresponding description in paragraphs [0070] to [0078] in US 2012/0065542 (published Mar. 15, 2012), incorporated herein by reference in its entirety.

Figure 2:
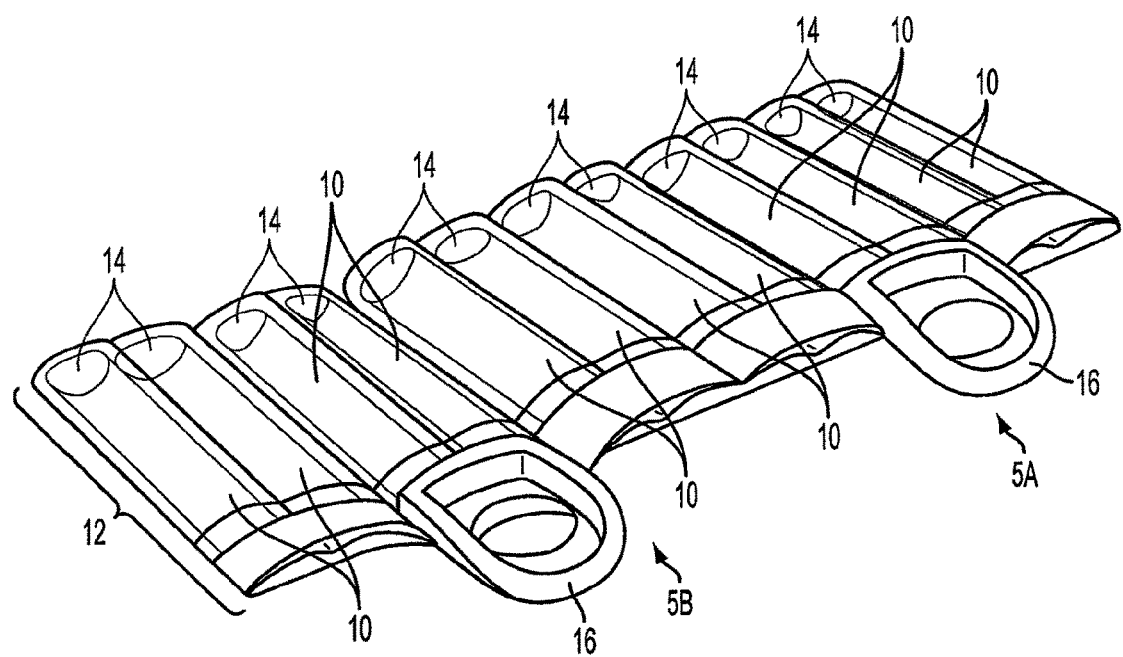
FIG. 2 illustrates an enlarged view of a pair of sample trays according to the first embodiment of the present application.

FIG. 2 illustrates an enlarged view of a pair of sample trays 5A, 5B. Sample tray 5A is substantially similar to sample tray 5B, and thus only sample tray 5A will be discussed in detail. Any differences between sample tray 5A and 5B will be noted. Though a pair of sample trays 5A, 5B are described in the present embodiment. However, an embodiment may use more or less than 2 trays 5A, 5B and all descriptions of a pair of trays 5A, 5B, should not be limited to requiring two trays, and may for example, include a single tray. Sample tray 5A comprises a plurality of sample containers 10, each sample container having a holding structure 12 configured to releasably hold a tissue sample collected during a biopsy procedure. Each holding structure 12 may have a sample access opening 14 through which tissue samples may enter or exit the holding structure 12.

In the embodiment shown in FIG. 2, the holding structure 12 consists of longitudinal sidewalls and two end walls defining a longitudinal chamber. In this embodiment, the sample access opening 14 may be formed through one of the end walls. Further, in this embodiment the holding structure 12 may be open on one of the sidewalls such that tissue samples may be viewed, and tactile examinations can be performed (i.e., a medical professional may touch) on the sample without removing the sample from the holding structure 12. The tissue samples from which the biopsy is taken can be bone, bone marrow, breast, cervical, joint, kidney, liver, lymph node, lung, pleural, prostate, small intestine, skin, synovial, thyroid, parathyroid, stomach, esophagus, oral cavity, pharynx, larynx, colon, rectal, anus, bladder, pancreas, spleen, central nervous system, peritoneum, genital, reproductive organ, heart and mediastinum. The present application may be useful when multiple samples are taken from a patient. Breast tissue is particularly amendable to use with VAB procedures. However, the holding structure 12 is not limited to this embodiment, and may have alternative structures. For example, the holding structure 12 may have a chamber, which is a cylindrical shape, ovoid shape, triangular shape, or any other shape sized to receive a biopsy core sample as would be apparent to a person of ordinary skill in the art. Further, the holding structure's sample access opening 14 may be formed in a sidewall or an end wall, or may have multiple sample access openings 14 formed in multiple end walls, longitudinal walls or both longitudinal and end walls. Further, although the holding structure 12 in FIG. 2 is open at on one sidewall, embodiments of the holding structure may be completely enclosed on all walls.

Each of the plurality of sample containers 10 which make up the sample tray 5A may be connected together by a joining member 16. The joining member 16 may connect the sample containers 10 along a portion or the whole of an end wall. The joining member 16 is preferably capable of being laid flat on a surface. In some embodiments, it is made of a flexible (or bendable) material. In other embodiments, it can be hinged between sample containers to allow it to flex. In the embodiment of FIG. 2, the sample containers 10 are only connected by a flexible joining member 16. The sample containers 10 may also be connected to each other along their length.

The sample trays 5A, 5B may be formed from a variety of materials and their construction is not particularly limited. The sample trays 5A, 5B may be constructed from a material that has one or more of the following features: transparent on imaging or with minimal interference (i.e. radio transparent), resistant to chemical fixatives (such as formalin), resistant to degradation from chemicals used in tissue processing (such as alcohol, xylene or acids), resistant to temperatures used in tissue embedding, and sectionable (e.g. with a microtome). Exemplary materials for forming the sample trays 5A, 5B include thermoplastic materials, including polyolefins (e.g., polyethylene, polypropylene, Teflon, etc.), polycarbonate, polystyrene, polyacetals, polyesters, polyamides (e.g. nylon), polyurethanes, silicone, and copolymers thereof (e.g. FEP) and combinations thereof.

Figure 3:
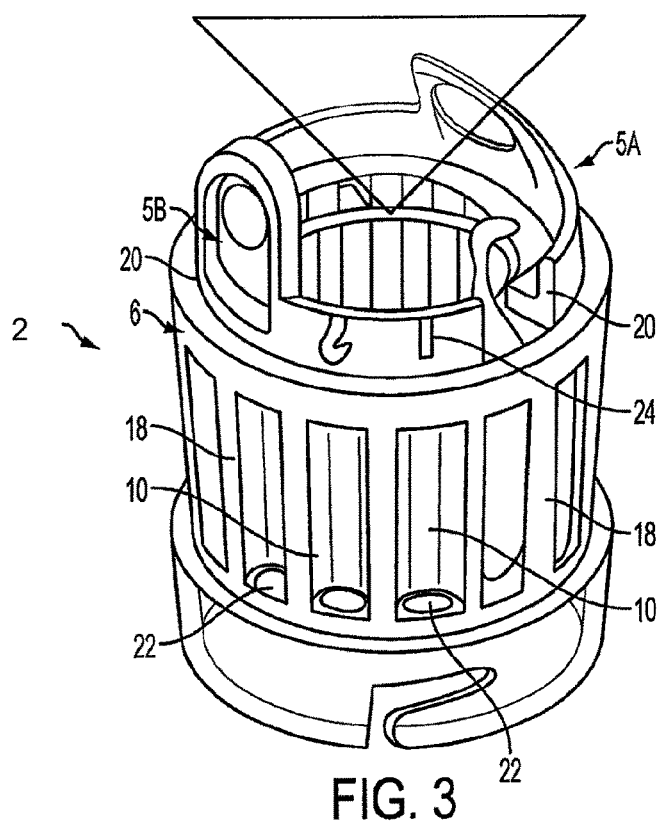
FIG. 3 illustrates an enlarged view of a tissue storage assembly according to the first embodiment of the present application.

FIG. 3 illustrates an enlarged view of the tissue storage assembly 2, which comprises at least one sample tray 5A, 5B and a bracing member 6. The bracing member 6 shown in FIG. 3 has a generally cylindrical shape, and comprises one or more chambers 18, which extend lengthwise through the bracing member 6. As shown in FIG. 3, the bracing member 6 also includes a first opening 20 formed at a topside of each of the chambers 18, and a second opening 22 formed at a bottom side of each of the chambers 18. Each of the chambers 18 of the bracing member 6 may receive one of the sample containers 10 of the sample trays 5A, 5B. Each of the sample containers 10 of the sample trays 5A, 5B may be inserted through each of the first openings 20 and into the corresponding chamber 18 of the bracing member 6. Further, the sample access openings 14 of each of the sample containers may be oriented downward to align with the second opening 22 formed a bottom side of each of the chambers 18.

The material used for the bracing member 6 is not particularly limited, and may include the same or different materials used to form the tray. In some cases, the bracing member is made from the same material as the tray and is manufactured as part of the tray. The bracing member may contain one or more tabs to allow the user to easily manipulate the tray out of the biopsy device and into the transport container.

FIG. 3 also illustrates that each of the sample containers 10 may be labeled with a unique identifier 24 which may allow each sample to be uniquely identified and distinguished during later testing.

Figure 4:
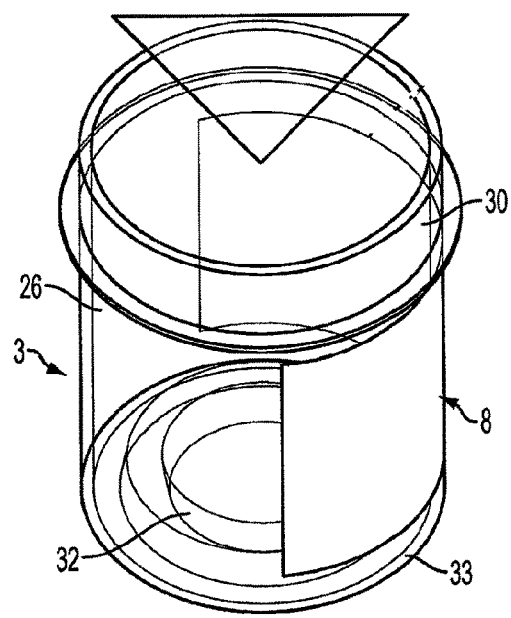
FIG. 4 illustrates an enlarged view of the housing and label according to the first embodiment of the present application.

FIG. 4 illustrates an enlarged view of the housing 3 and label 8. In FIG. 4, the housing is generally cylindrical in shape and includes a sidewall 26 and an assembly insertion opening 28. The assembly insertion opening 28 is configured to allow the tissue storage assembly 2 to be inserted into the interior of the housing. More specifically, the assembly insertion opening 28 is sized and shaped so that the tissue storage assembly 2 can pass easily into the interior of the housing. Further, a closing portion 30 may be disposed proximate to the assembly insertion opening 28, and the closing portion 30 may interact with the lid 4 (not shown) to seal and close the assembly insertion opening 28. The closing portion 30 may be a threaded fitting, a pressure fitting, or any other fitting capable of sealing with a lid to prevent liquid leakage as would be apparent to a person of ordinary skill in the art.

Further, the housing 3 may also have a sealing member 32 configured to interact with the tissue storage assembly 2 to block the sample access openings 14 of the individual sample containers 10 of the sample trays 5A, 5B. Specifically, the sealing member 32 may cover the openings or may include one or more protrusions which extend upward from a surface of the sealing member and are sized and shaped to be inserted through the second openings 22 formed in the bottom of the bracing member 6, and into each of the sample access openings 14 of the individual sample containers 10 of the sample trays 5A, 5B.

Alternatively, the sealing member 32 may include a single protrusion configured to engage and seal multiple sample access openings 14 of multiple individual sample containers 10 of the sample trays 5A, 5B. The size and shape of the protrusions are not particularly limited, may be any size and shape which can create a sufficient seal with the sample access openings 14 of the individual sample containers 10 of the sample trays 5A, 5B to prevent tissue samples from falling out of the sample trays 5A, 5B. For example, the sealing member may be annularly shaped as shown in FIG. 4.

The sealing member 32 may be removably affixed to the bottom of the housing 3 such that it can be transferred to the at least one tray 5A, for example. For example, one or more of the protrusions on the sealing member 32 may engage the sample access opening 14 of one of the individual sample containers 10 of a tray 5A, attaching to the tray and releasing from the bottom of the housing. Such removable attachment may be achieved using mechanical means such as a tongue and groove configuration, a releasable tab configuration, or any other configuration of removably attaching the sealing member 32 to the housing 3. Alternatively or additionally, the removable attachment may be achieved using an adhesive which degrades upon adding fixing agent to the housing to preserve the samples.

Additionally, the housing 3 may also include a bottom 33 disposed on a side of the housing opposite the assembly insertion opening 28. In some embodiments, the bottom may be removable to form an assembly removal opening (not shown) to allow the assembly to be removed through. In FIG. 4, the assembly removal opening would be disposed at the bottom of the cylindrical housing 3. The assembly removal opening may be sized and shaped so that the tissue storage assembly 2 can pass easily out of the interior the housing 3. By providing a separate assembly insertion opening 28, the closing portion 30 may be configured to lock the lid 4 (not shown) in place upon sealing such that the lid could not be reopened once sealed. Further, by providing an assembly removal opening 29 at the bottom of the housing, the tissue samples may be removed through the bottom of the housing 3.

Additionally, the sealing member 32 may be removably attached to the removable bottom which seals and closes the assembly removal opening 29.

The material of the housing 3, including the sealing member 32, and the lid 4 is not particularly limited and may include polymer materials, resin materials, and ceramic materials (e.g. plastics, resins, and ceramic/glass). Additionally, the material of housing 3 and lid 4 may be constructed from a material has one or more of the following characteristics: transparent on imaging or with minimal interference (i.e. radio transparent), resistant to chemical fixatives (such as formalin), resistant to degradation from chemicals used in tissue processing (such as alcohol, xylene or acids), and resistant to temperatures used in tissue embedding. Exemplary materials for forming the housing 3 and lid 4 may include thermoplastic materials, including polyolefins (e.g., polyethylene, polypropylene, Teflon, etc.), polycarbonate, polystyrene, polyacetals, polyesters, polyamides (e.g. nylon), polyurethanes, silicone, and copolymers thereof (e.g. FEP) and combinations thereof.

FIG. 4 also shows the label 8 which may be attached to the housing 3. The label 8 may be a human and/or computer readable label upon which information about the patient, the collected sample, and collection conditions may be retained. The information retained with the sample can comprise one or more of patient name, patient accession number, business address information, hospital address information, social security number information, patient medical history information, date information, biopsy time information, location information (e.g. location within a patient (e.g. duct or lobule in breast), within a targeted biopsy site, relative to the position of another biopsy sample, or relative to a biopsy marker located within a patient), and the time that the fixative is contacted with sample. Additional information retained may also include pH of fixing solution at time of fixation of the sample, and temperature of fixation solution, etc. Additionally, the label may include unique identifying information for each of the plurality of samples being transported.

In some embodiments, the label 8 may be a computer readable tag or label including, but not limited to, labels having an incorporated RFID tag, labels having an incorporated one-dimensional (1-D barcode), two-dimensional barcode (2-D barcode), and labels having an incorporated three-dimensional barcode (3-D barcode). However, the computer readable label is not limited to RFID, 1-D barcode, 2-D barcode, or 3-D barcode labels and may include any type of label readable by a computer as would be apparent to a person of ordinary skill in the art.

In some embodiments, more than one tag may be present. When more than one tag is present, they can be physically separated or located together. In one embodiment, a tag may be associated with each holding structure or a group of holding structure so that if the holding structures are later detached from each other, a tag remains with each sample or group of samples.

In some embodiments, a tag is present that may be sensitive to changes to the sample or to the tray itself. For example, a tag may be present that changes physical (i.e. color) or chemical (i.e. redox, conjugation, etc.) properties during fixation of the sample. Similarly, a tag may be present that is sensitive to the processing steps which precede embedding (i.e. dehydration). Alternatively, a tag may be present that is sensitive to the embedding step (i.e. infiltration of wax). The tag may have a property that changes incrementally or switches when the step is complete. In this way, the technician, or an automated system, will be able to determine when the sample has finished one step before another is started.

In another embodiment, a tag may be present that directs processing of the tissue in a tissue processor (such as a PELORIS or ASP systems available from LEICA, Wetlzar Germany). For example, the tag may direct a tissue processing unit to use a protocol designed for fatty breast tissue versus muscle tissue.

In FIGS. 1 through 4, the label 8 is shown attached to the housing 3, but embodiments of the present application are not limited to the label being attached to the housing. Embodiments of the present application may include the label 8 being attached to one or more of the tissue storage assembly 2 (the tray 5A, 5B, the bracing member 6, or individual sample containers 10), the lid 4, or the housing 3.

Fixing Agent Handling Components

As discussed above, in order to preserve the one or more collected biopsy tissue samples for subsequent histological analysis, it is necessary to perform a fixation process on the sample (i.e. submerging the sample in a bath of fixation solution). Typical fixation techniques include, fixation in acetone, methanol, ethanol, methanol acetone (e.g., fix in methanol, remove excess methanol, permeabilize with acetone), methanol-acetone mix (e.g., 1:1 methanol and acetone mixture), methanol-ethanol mix (e.g., 1:1 methanol and ethanol mixture), formalin, paraformaldehyde, gluteraldehyde, Histochoice, Streck cell preservative (Streck Labs., Nebraska), Bouin's solution (a fixation system containing picric acid), Sed-Fix (a polyethylene glycol based fixation system available from Leica Biosystems, Buffalo Grove Va.), FineFix (Leica Biosystems, Buffalo Grove Va.), Carnoys, Modified Carnoys/Clarkes solution, Ethanol, FineFX, Methacarn, Methanol, Molecular Fixative (UMFIX), Boon-Fix, Polyethylene glycol based fixatives, RCL2, Uni-Fix, Glyco-Fix, Gluteraldehyde, HistoCHOICE, HistoFix, HOPE Fixation, Ionic liquid, Mirsky's fixative, NOTOX-histo, Prefer, Preserve, Zenker or any other fixing agent as would be apparent to a person of ordinary skill in the art.

In some embodiments, the fixative may be poured into the container before sealing. In some embodiments, the fixative may be provided as a tablet or powder and be added to the container and then rehydrated with water. However, at least some of these fixing solutions pose moderate to severe risks to humans, and thus must be handled with care. Thus, some embodiments of the present application may include fixing agent handling components which may reduce the need for a person to directly handle a fixing solution by maintaining the fixing solution (or a dehydrated powder or tab) in a sealed area, and releasing the fixing solution into the transportation device in response to a specific action.

Figure 5:
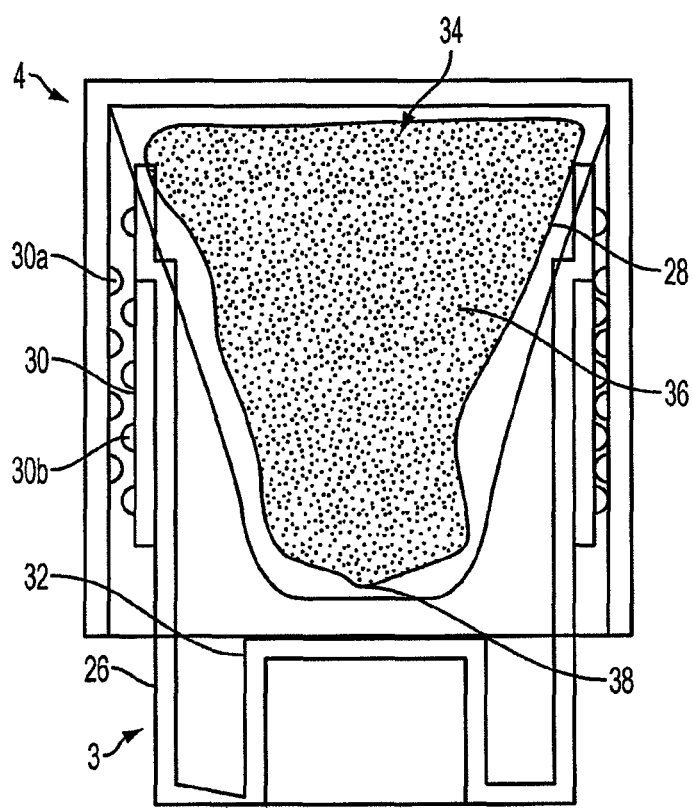
FIG. 5 illustrates a side view of a biopsy tissue sample transport device having a fixing agent pouch according to the first embodiment of the present application in a closed and empty state.
Figure 6:
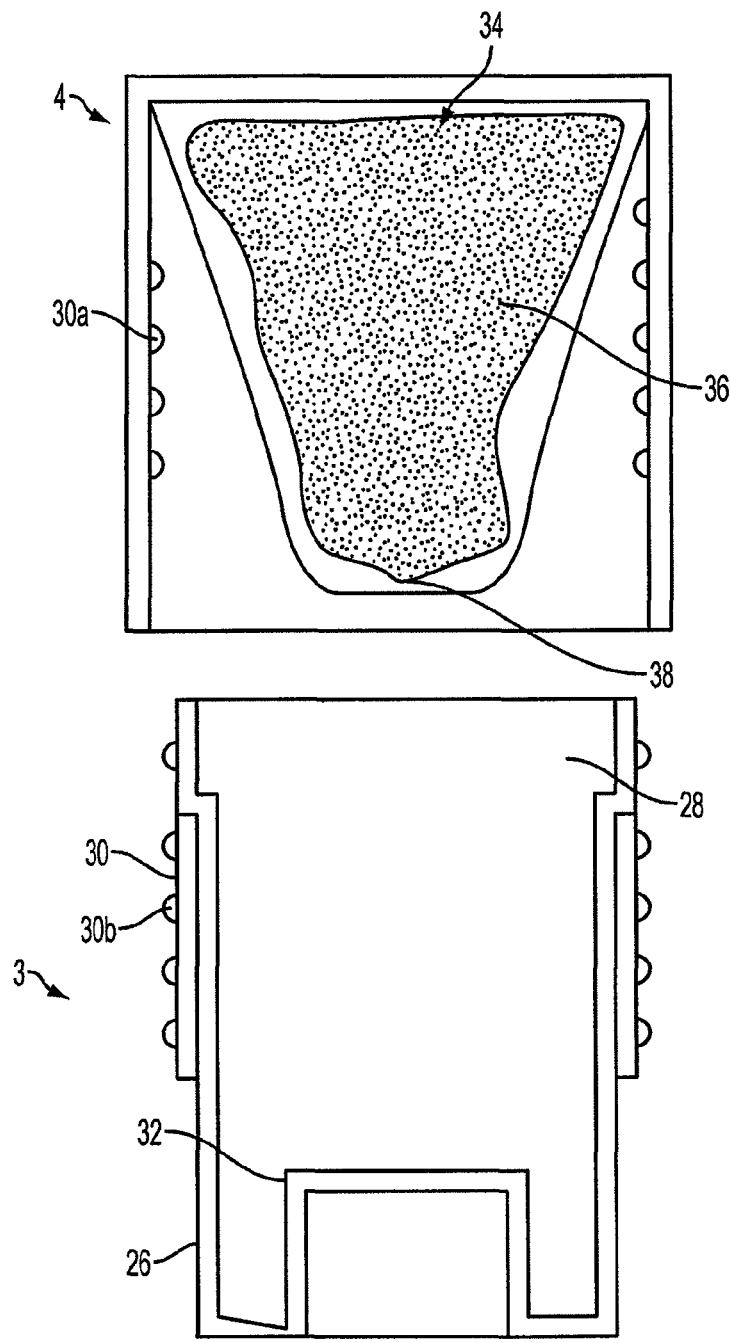
FIG. 6 illustrates a side view of the biopsy tissue sample transport device having a fixing agent pouch according to the first embodiment of the present application in an open and empty state.

FIG. 5 illustrates a side view of a biopsy tissue sample transport device having a fixing agent pouch according to the first embodiment of the present application in a closed and empty state. FIG. 6 illustrates a side view of the biopsy tissue sample transport device having a fixing agent pouch according to the first embodiment of the present application in an open state. FIGS. 5 and 6 illustrate an embodiment of a transportation device similar to the first embodiment discussed above, further including a fixing agent pouch 34 disposed in a lid 4 designed to engage the housing 3. Again, the housing 3 includes a sidewall 26, a tissue storage assembly insertion opening 28, a closing portion 30 and a sealing member 32.

Further, as shown in FIG. 5, the closing portion 30 is a threaded region comprising a plurality of threads 30a which engage a plurality of threads 30b of the lid 4 to seal the lid 4 to the housing 3.

The fixing agent pouch 34 may be filled with a fixing solution 36, which will preserve any tissue samples stored in the housing 3. Further, the fixing agent pouch 34 also has a frangible portion 38, which is designed to be broken or ruptured to allow the fixing solution 36 be released into the housing 3 based on a specific action. The frangible portion 38 may be a perforated region or a region formed of a material from the remainder of the fixing agent pouch 34, such that the fixing agent pouch 34 can be caused to break in a predictable manner.

Figure 7:
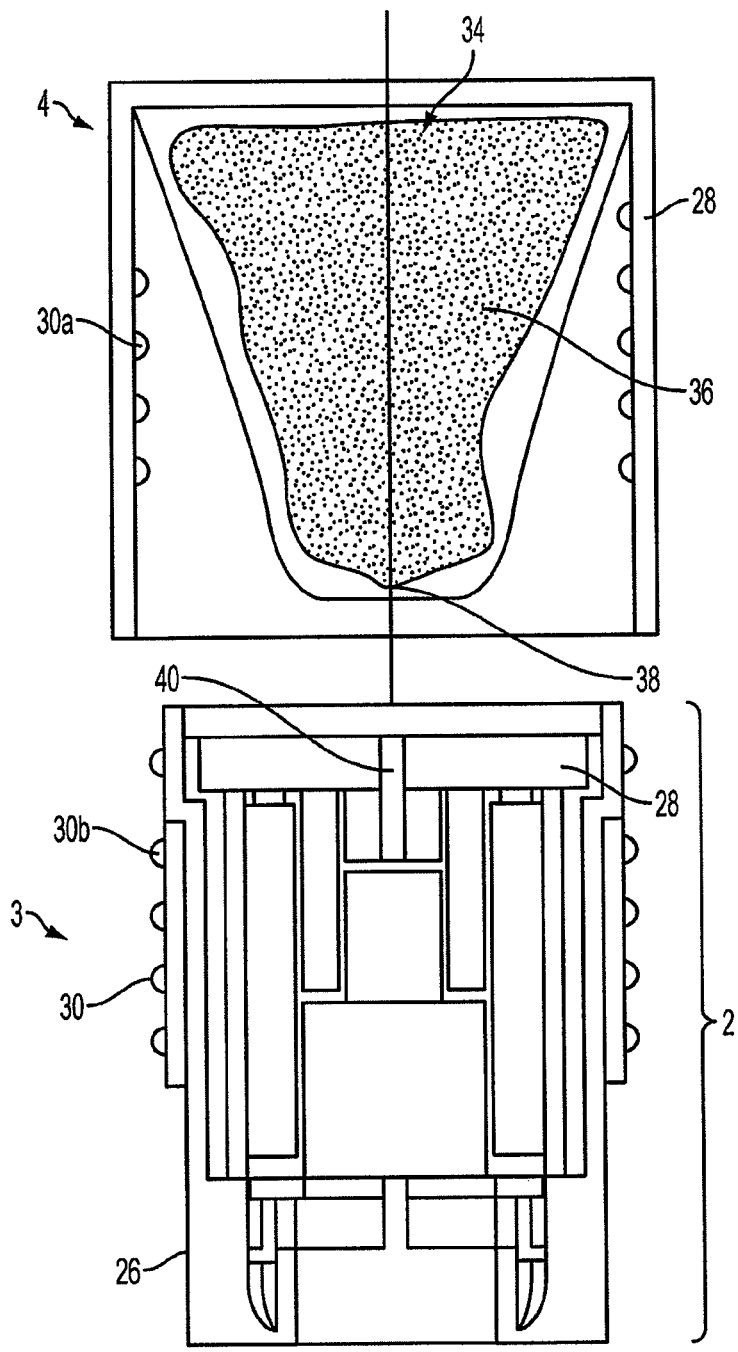
FIG. 7 illustrates a side view of the biopsy tissue sample transport device having a fixing agent pouch according to the first embodiment present application in an open state and containing a tissue storage assembly.

FIG. 7 illustrates the embodiment of the transportation device with the fixing agent pouch 34 disposed to lid 4 with a tissue storage assembly 2 inserted through the tissue storage assembly insertion opening 28 and into the housing 3. Further, a breaking member 40 is also disposed within the housing 3. In FIG. 7, the breaking member 40 is a needle shaped member configured to engage the frangible portion 38 of the fixing agent pouch 34 upon closing and sealing of the lid 4 to the housing 3. Specifically, the needle shaped breaking member 40 is oriented to point upward, and the fixing agent pouch 34 is suspended from the lid 4 such that the frangible portion 38 is oriented downward. As the lid 4 is lowered onto the housing 3, the frangible portion 38 of the fixing agent pouch 34 is forced downward onto the pointed end of the breaking member 40. As the closing portion 30 engages the lid 4, additional force is exerted on the frangible portion 38 by the breaking member 40 causing the frangible portion 38 to rupture and release the fixing agent 36 into the housing and submerge the biopsy tissue samples stored in the tissue storage assembly 2. The volume of fixing solution 36 provided is chosen to be sufficient to fill housing 3 such that the biopsy tissue samples in the sample trays 5A, 5B are submerged.

Further, in the above embodiment, the breaking member 40 is needle shaped and oriented upward, and the frangible portion 38 of the fixing agent pouch 34 is located at a bottom side of the fixing agent pouch 34. However, the breaking member 40 is not limited to a needle shaped nor must it be oriented upward. Further, the frangible portion 38 of the fixing agent pouch 34 need not be located at a bottom side of the fixing agent pouch 34, but may be located anywhere on the fixing agent pouch 34 or the entire fixing agent pouch 34 may be frangible. An embodiment of the breaking member 40 and the fixing agent pouch 34 may have any alternative orientation as would be apparent to a person or this coming.

Embodiment 2

Figure 8:
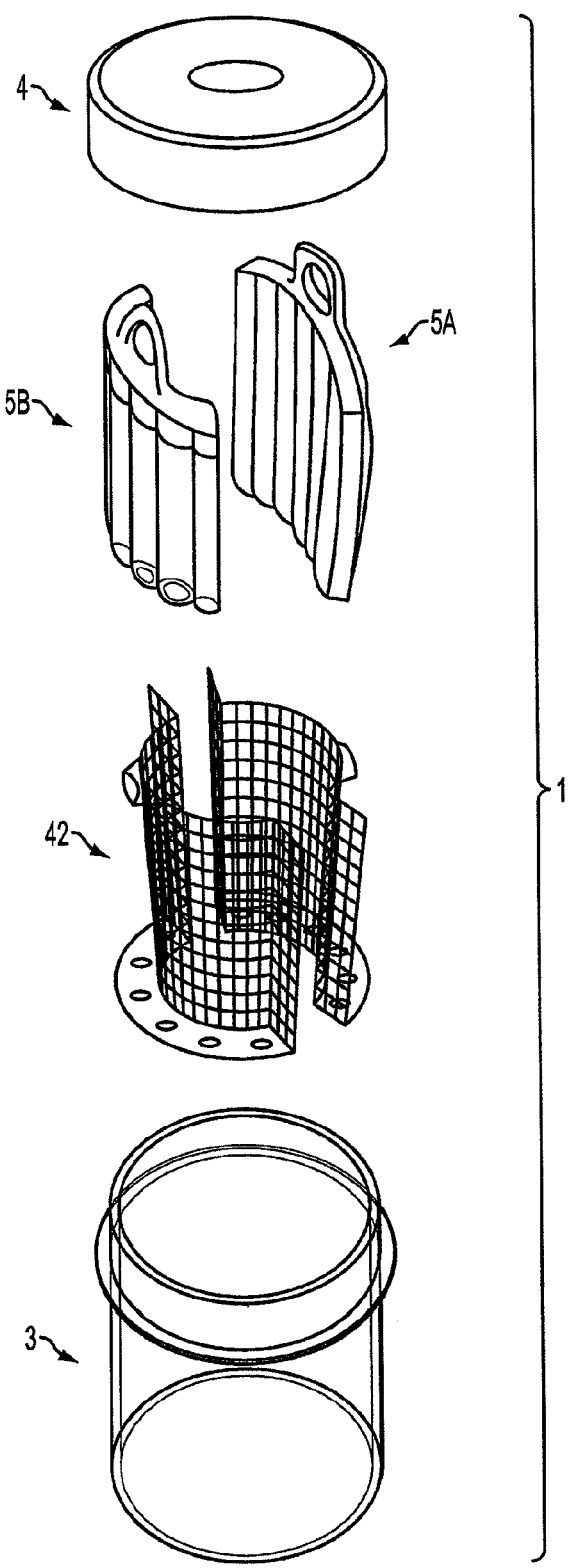
FIG. 8 illustrates an exploded view of a biopsy tissue sample transport device according to a second embodiment of the present application.

FIG. 8 illustrates an exploded view of a biopsy tissue sample transport device 1 according to a second embodiment of the present application. The biopsy tissue sample transport device 1 of this embodiment mirrors the embodiment described above having a housing 3 and a lid 4. However, this embodiment includes a tissue storage assembly 2 with at least one sample tray 5A, 5B, but does not include a bracing member 6. The sample trays 5A, 5B of the tissue storage assembly were discussed in detail above with respect to FIG. 2 above and redundant discussion is omitted. The biopsy tissue sample transport device 1 of this embodiment also includes one or more holding members 42 configured to engage and seal one or more of sample containers 10 of the sample trays 5A, 5B. The holding members 42 are discussed in more detail below with respect to FIG. 9.

Figure 9:
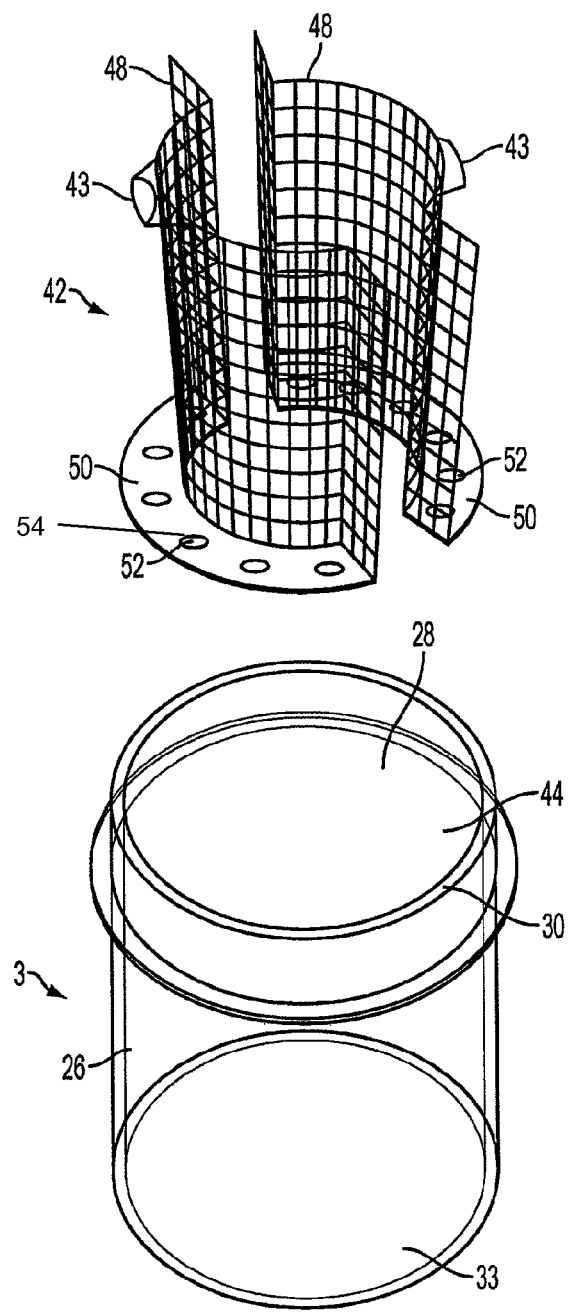
FIG. 9 illustrates an enlarged view of the housing and holding member according to the second embodiment of the present application.

FIG. 9 illustrates an enlarged view of the housing 3 and holding member 42. In FIG. 9, the housing 3 is similar to the embodiment described above and is generally cylindrical in shape and includes a sidewall 26 and an assembly insertion opening 28. Further, the housing 3 may also include an interior region 44 which may include one or more longitudinally extending slots 46 (example embodiments of the longitudinal slots 46 are shown in FIGS. 10 through 13), each slot may be sized and shaped to receive one or more of the sample containers 10 of the sample trays 5A, 5B. In some embodiments, this longitudinal slot 46 extends the length (i.e. height) of the housing 3 such that each of the sample containers is held in an upper right orientation. Further, the longitudinal slot 46 may have an arc shape (shown in FIG. 12) extending at least partially along a circumferential direction of the cylindrical housing.

Further, similar to the embodiment above the closing portion 30 may be disposed proximate to the assembly insertion opening 28, and the closing portion 30 may interact with the lid 4 (not shown) to seal and close the assembly insertion opening 28. The closing portion 30 may be a threaded fitting, a pressure fitting, or any other fitting capable of sealing with a lid to prevent liquid leakage as would be apparent to a person of ordinary skill in the art.

Further, one or more holding members 42 may be inserted into the housing 3. Each holding member 42 may include a longitudinal portion 48 and a horizontally extending portion 50 attached at one end of the longitudinal portion. Each holding member 42 may have an arc shape, which is sized and shaped to conform to the arc shape of the longitudinally extending slot 46 of the housing 3 such that the longitudinal portion 48 of the holding member 42 extends along the sidewall of the slot 46 in a horizontal portion 50 rests at a bottom of the arc shaped slot 36. However, the holding member 42 is not limited to an arc shape, and may have any shape which fits into the slot 46 of the housing 3.

Each holding member 42 may be configured to interact with the tissue storage assembly 2 to seal the sample access openings 14 of the individual sample containers 10 of the sample trays 5A, 5B (similar to the sealing member disclosed in Embodiment 1). Specifically, the holding member 42 may include one or more holding portions 52. The holding portions may be flat regions or may be protrusions 54, which extend upward from a surface of the holding member 42. Each protrusion 54 may be sized and shaped to block access to or to be inserted into each of the sample access openings 14 of the individual sample containers 10 of the sample trays 5A, 5B.

Alternatively, the holding member 42 may include a single protrusion 54 configured to engage and seal multiple sample access openings 14 of multiple individual sample containers 10 of the sample trays 5A, 5B. The size and shape of the protrusions are not particularly limited, and may be any size and shape which can create a sufficient seal with the sample access openings 14 of the individual sample containers 10 of the sample trays 5A, 5B to prevent tissue samples from falling out of the sample trays 5A, 5B.

The holding member 42 may be removably affixed to the bottom of the slots 46 of the housing 3 such that when one or more of the protrusions engages the sample access opening 14 of one of the individual sample containers 10, the holding member 42 becomes attached to the sample container 10 or sample tray 5A, 5B. For example, in FIG. 9 a tab 43 is provided at one end of each of the holding members 42 and the tab 43 is configured to engage one of the sample trays 5A, 5B, after the sample tray 5A, 5B is inserted into the slot 46 of the housing 3.

The removable attachment between the holding member 42 and housing 3 may be achieved using mechanical means such as a tongue and groove configuration, a releasable tab configuration, or any other configuration of removably attaching the holding member 42 to the housing 3. Alternatively, the removable attachment may be achieved using an adhesive which degrades upon adding fixing agent to the housing to preserve the samples.

Figure 10:
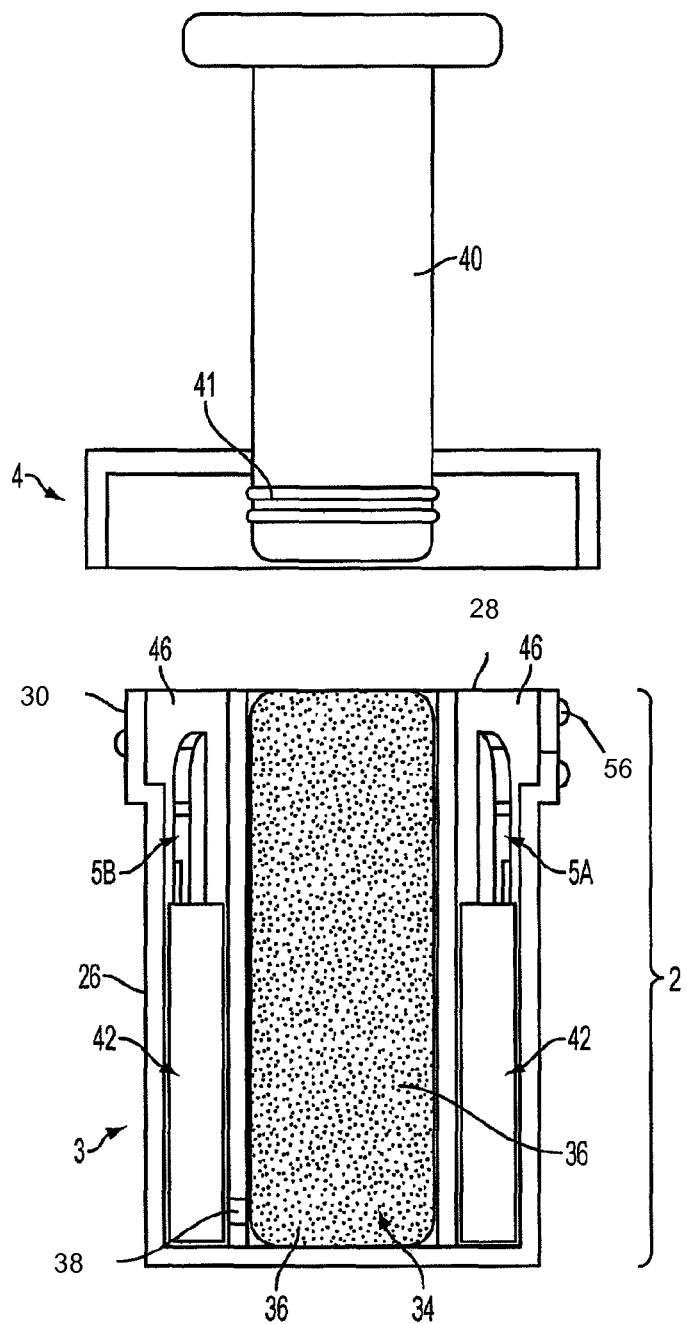
FIG. 10 illustrates a side view of a biopsy tissue sample transport device having a fixing agent pouch according to the second embodiment of the present application in an open state.
Figure 11:
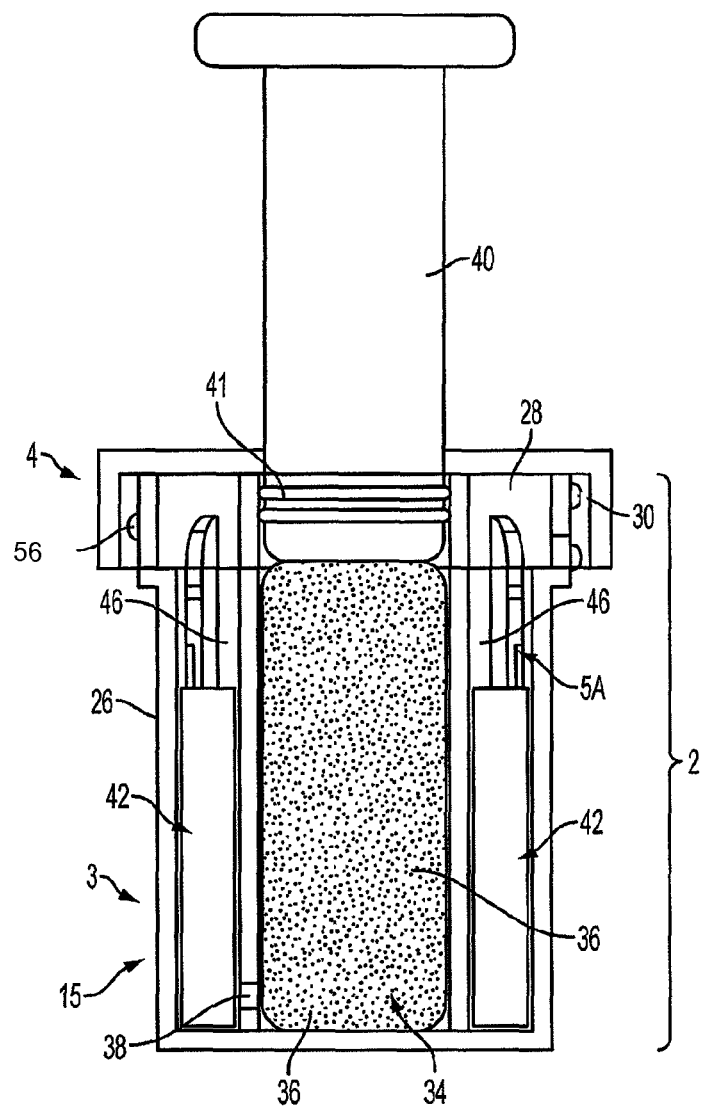
FIG. 11 illustrates a side view of a biopsy tissue sample transport device having a fixing agent pouch according to the second embodiment of the present application in a closed state with the breaking member withdrawn.
Figure 12:
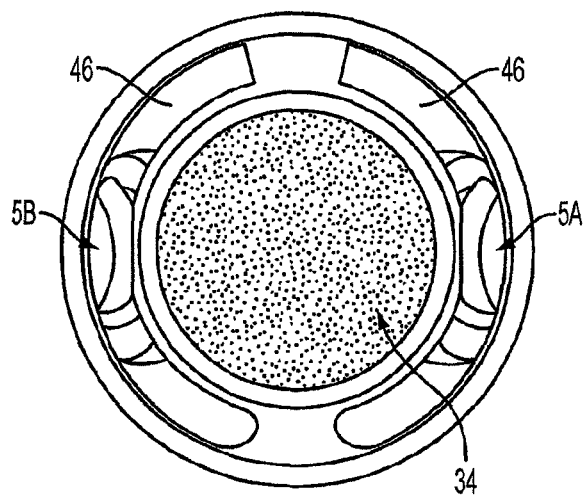
FIG. 12 illustrates a top view of the housing 3 of a biopsy tissue sample transport device having a fixing agent pouch according to the second embodiment of the present application in an open state.

The fixing agent pouch may also be disposed within the lid 4 similar to the fixing agent pouch described above with respect to the first embodiment without significant modification. Alternatively, FIGS. 10-13 illustrate the fixing agent pouch 34 disposed within the housing 3. FIG. 10 illustrates the housing 3 and the lid 4 in a pre-sealed configuration. FIG. 11 illustrates the housing 3 and the lid 4 in a sealed configuration. FIG. 12 illustrates a top view of the housing 3 prior to sealing of the lid 4 to the housing 3.

In FIG. 10, pair of tissue storage trays 5A, 5B, which form a tissue storage assembly 2, have been inserted into the pair of longitudinally extending slots 46, and each tray 5A, 5B has engaged a holding member 42.

In this embodiment, the closing member 30 includes a plurality of threads 56 configured to engage the lid 4 to form a seal. Further, in this embodiment the housing 3 also includes a central cylindrical region. The fixing agent pouch 34 is disposed within the central cylindrical region. The fixing agent pouch 34 is filled with a fixing solution 36, and includes a frangible portion 38 configured to rupture and release the fixing solution 36 into the housing in response to a specific action.

In this embodiment, the lid 4 includes a breaking member 40. In this embodiment the breaking member 40 is a plunger member configured to engage the top surface of the fixing agent pouch 34 when the lid 4 is sealed to the housing 3. A sealing 41 may be formed at one end of the breaking member 40 to prevent fluid leakage around the breaking member 40 and provide a leak-proof seal in the lid 4. When the lid 4 is sealed to the housing 3, the breaking member 40 rests on top of the fixing agent pouch 34 and is substantially aligned with the central cylindrical region of the housing 3.

Figure 13:
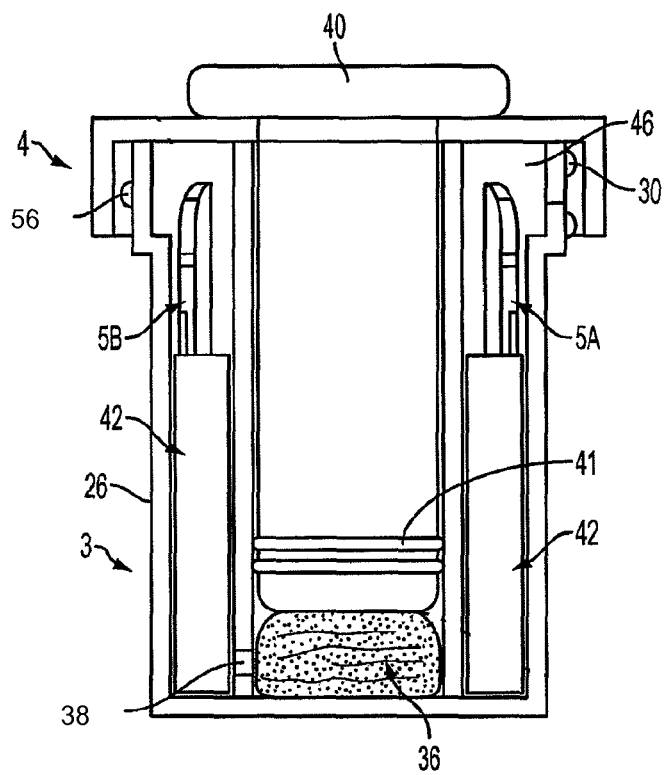
FIG. 13 illustrates a side view of a biopsy tissue sample transport device having a fixing agent pouch according to the second embodiment of the present application in a closed state with the breaking member fully inserted.

FIG. 13 illustrates the effect of pressing the plunger shaped breaking member 40 through the lid 4 and into the central cylindrical region of the housing 3. As the breaking member 40 is pressed downward, a squeezing force is applied to the fixing agent pouch 34 increasing the pressure of the fixing solution 36. When the pressure of the fixing solution 36 exceeds a breaking strength of the frangible portion 38, the frangible portion 38 ruptures and the fixing solution 36 is forced out of the central cylindrical region and into the longitudinally extending slots 46. The volume of fixing solution 36 provided is chosen to be sufficient to fill the longitudinally extending slots 46 such that the biopsy tissue samples in the sample trays 5A, 5B are submerged.

Though the above discussed embodiment shows a fixing agent pouch disposed within housing 3 of a tissue transport device consistent with the second embodiment of figures, a fixing agent pouch may also be disposed within the housing 3 of the first embodiment, without significant modification.

Further, in the above embodiment, the breaking member 40 is a plunger shaped member and is oriented downward, and the fixing agent pouch 34 is located in a central region of the housing 3. However, the breaking member 40 and fixing agent pouch 34 need not have this configuration. For example, the fixing agent pouch 34 may be disposed within the lid 4 of the transportation device, and an upward facing protruding member may be disposed within the housing, such that the act of pressing the lid 4 onto the housing 3 causes the fixing agent pouch to be compressed by the upward facing protruding member, thereby squeezing fixing agent solution out of the pouch and into the remainder of the housing.

Further, the frangible portion 38 of the fixing agent pouch 34 need not be located at a bottom side of the fixing agent pouch 38, but may be located anywhere on the fixing agent pouch 34 or the entire fixing agent pouch 34 may be frangible. An embodiment of the breaking member 40 and the fixing agent pouch 34 may have any alternative orientation as would be apparent to a person of ordinary skill in the art.

Embodiment 3

Figure 14:
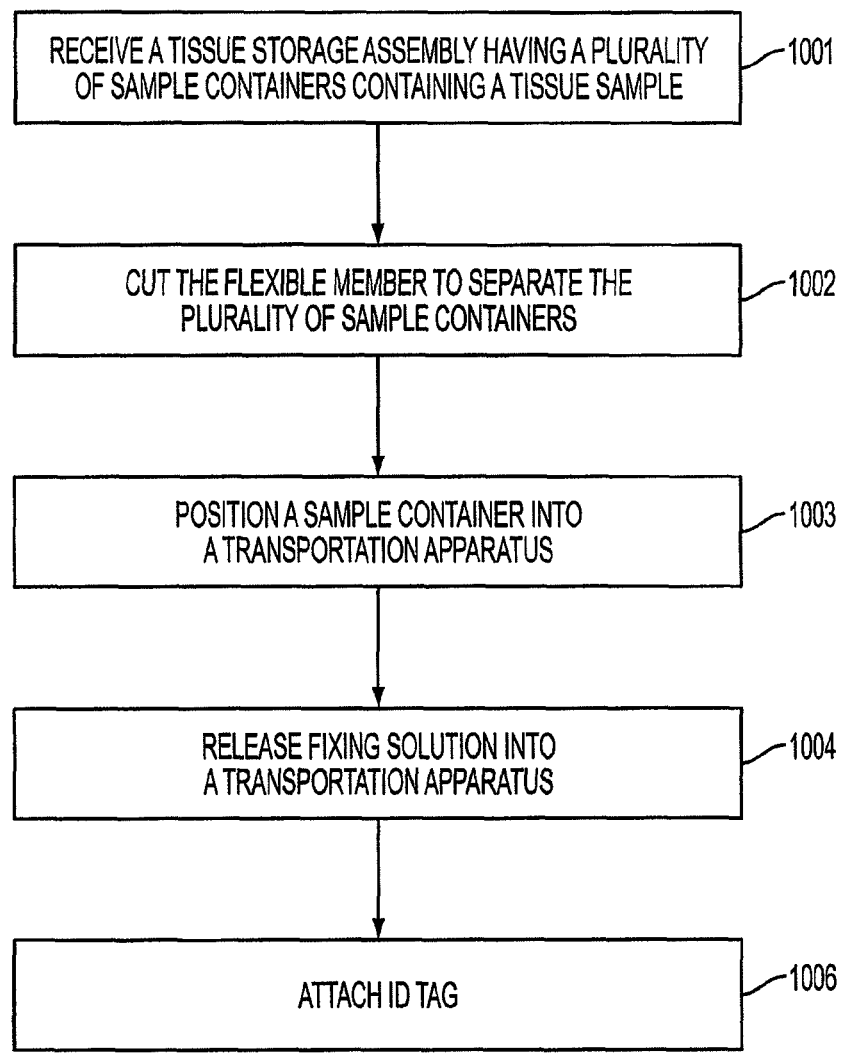
FIG. 14 illustrates a flowchart showing a method for preparing a tissue sample for transport according to a third embodiment of the present application.

A third exemplary embodiment is disclosed with respect to FIGS. 14-21. FIG. 14 illustrates the steps involved with using the transport device involved with this embodiment. This embodiment mirrors the previous embodiments, however, after receiving a tissue storage assembly 2 similar to the one disclosed above (step 1001), the trays 5A, 5B are separated from the joining member 16 (step 1002) and held by a processing cassette 60, which inserts into the housing 3 and is closed by the lid 4 (step 1003).

Figure 15:
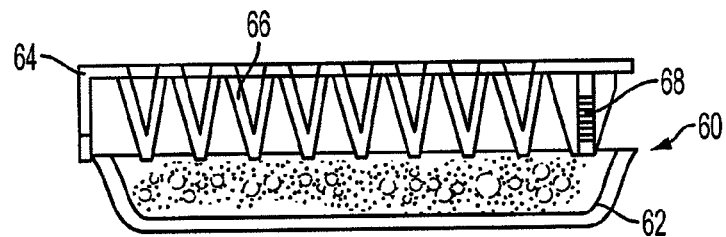
FIG. 15 illustrates an enlarged view of a transport cassette according to the third embodiment of the present application.

FIG. 15 illustrates an example of the processing cassette 60. The processing cassette 60 includes a cassette housing 62, and a cassette lid 64. The cassette lid 64 may include a holding structure 66 to hold the tissue sample in place and maintain its orientation during subsequent processing. Further, the cassette lid 64 also includes a latching member 68 to hold the cassette 60 closed. The attachment between the cassette lid 64 and a cassette housing 62 of the cassette 60 is not particularly limited, and may include a hinge structure, a snap fit structure, or any other structure to hold the cassette lid 64 to the cassette housing 62 as would be apparent to a person of ordinary skill in the art.

Figure 16:
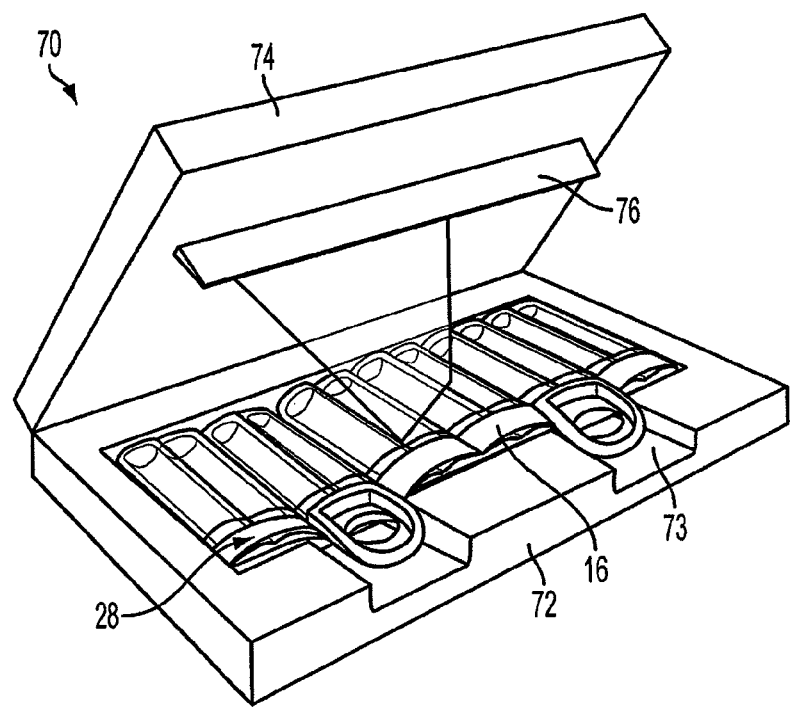
FIG. 16 illustrates a cutting jig used in the third embodiment of the present application.

FIG. 16 illustrates an example embodiment of a cutting jig 70 used to cut the joining member 16 and separate the plurality of sample containers 10. The cutting jig 70 includes a bottom member 72 and a top member 74. The bottom member 72 has a recess 73 shaped and sized to receive one or more of the sample trays 5A, 5B. Further, a cutting element 76 is mounted to the top member 74 and aligned with the assembly insertion opening 28 of the joining member such that when top member 74 is brought down toward the bottom member 72, the cutting element 315 cuts through the joining member 16.

Figure 17:
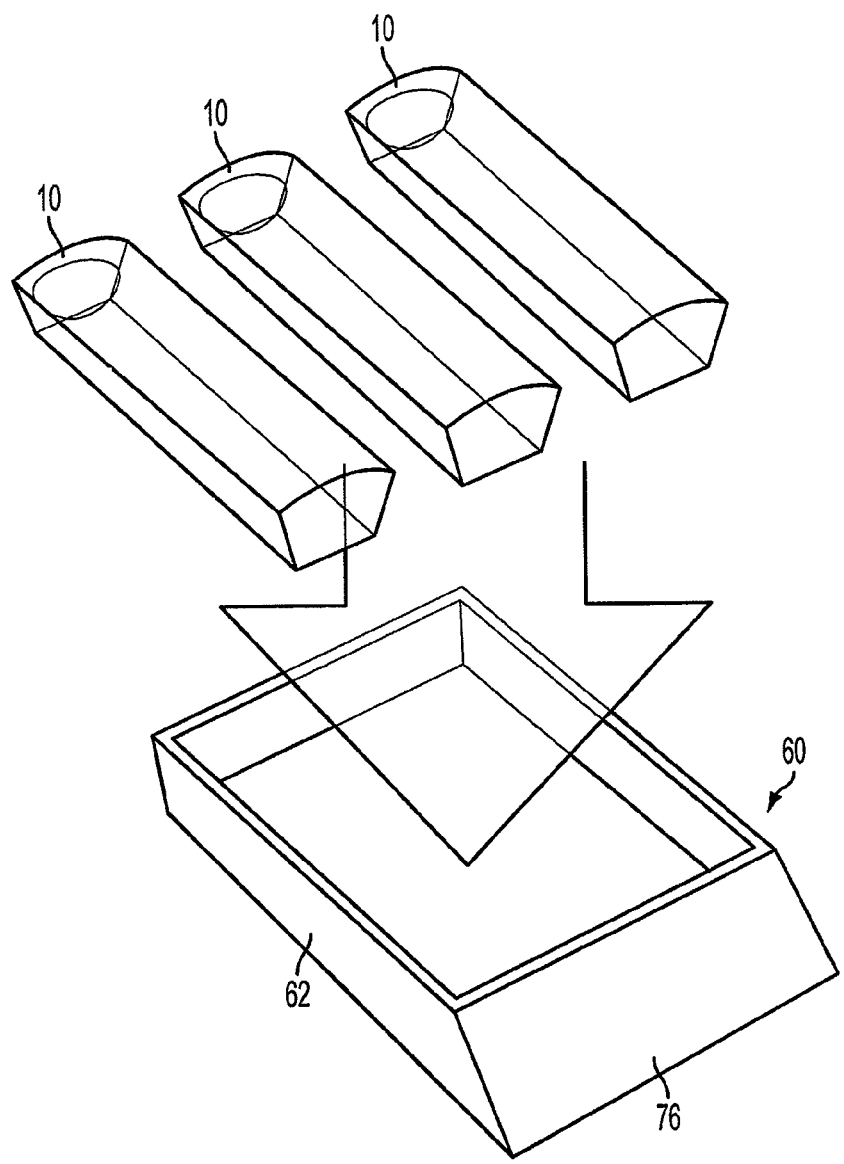
FIG. 17 illustrates positioning one or more sample containers in a transport cassette according to the third embodiment of the present application.

After the sample containers 10 are separated they are placed in a cassette 60. FIG. 17 illustrates an example of three of the individual sample containers 10 being inserted into the housing 18 of the processing cassette 60. As shown in FIG. 17, the sample containers 10 are aligned such that the biopsy core samples are relatively parallel to each other and are inserted into the cassette housing 62 of the cassette 60. FIG. 17 also shows that in some embodiments the processing cassette housing 62 of the cassette 60 may also include an inclined portion 76 formed at one end. After the sample containers 10 are inserted into the cassette housing 62, the cassette lid 64 (shown in FIG. 15) may be closed to secure the sample containers 10 within the cassette 60.

Figure 18:
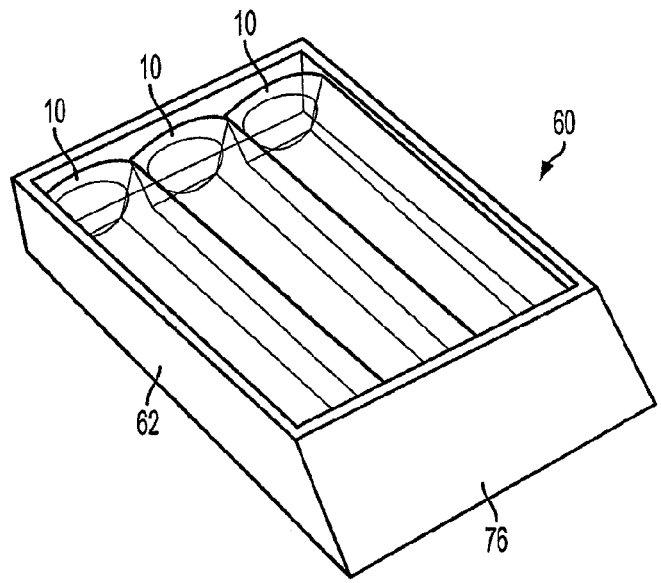
FIG. 18 illustrates one or more sample containers position in a transport cassette according to the third embodiment of the present application.
Figure 19:
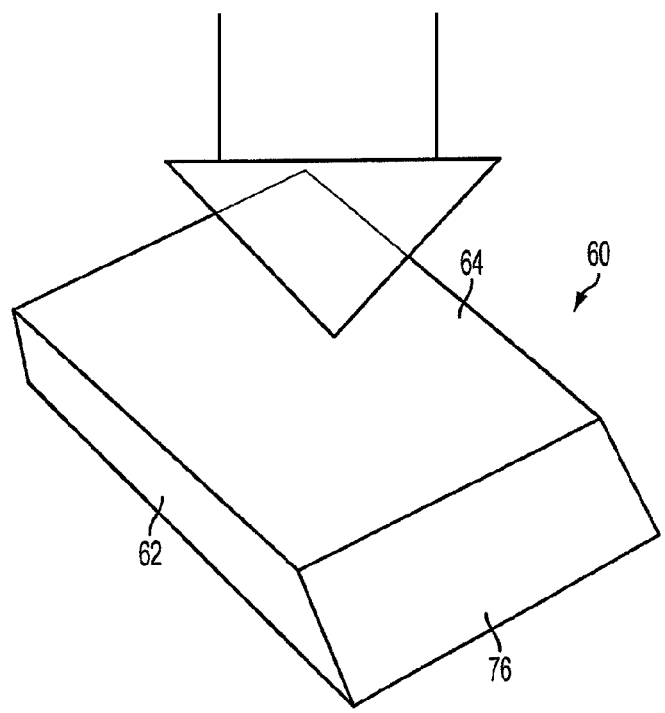
FIG. 19 illustrates a closed transport cassette according to the third embodiment of present application.

FIG. 18 illustrates the cassette 60 after three sample containers 10 have been inserted into the cassette housing 62. FIG. 19 illustrates the cassette 60 after the cassette lid 64 has been attached to close the cassette 60. After the cassette lid 64 has been closed, the sample containers 10 are enclosed within the cassette housing 62.

It should be noted that in the embodiment discussed above, a separate cutting jig 70 is used to cut the joining member 16 and after the joining member 16 is cut, the sample containers 10 are positioned in the cassette 60. However, these events need not occur in the sequence and a separate cutting jig 70 is not required.

Figure 20A:
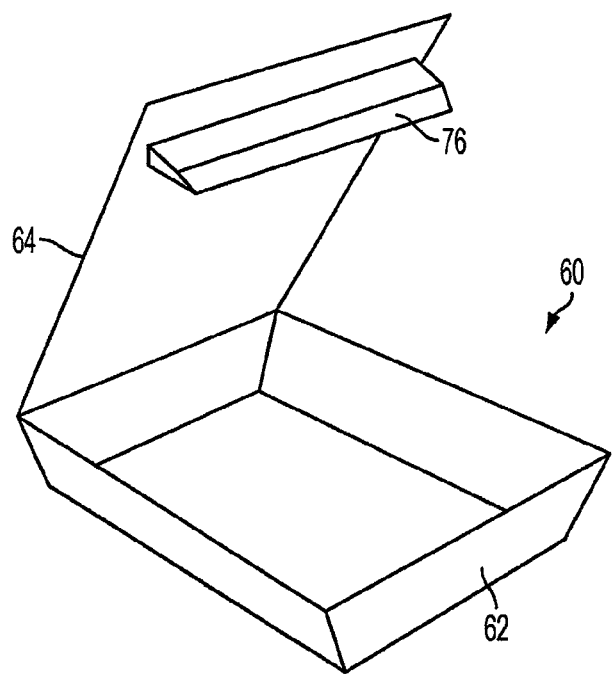
FIGS. 20A and 20B illustrates a transport cassette having an incorporated cutting element according to another embodiment of the present application.
Figure 20B:
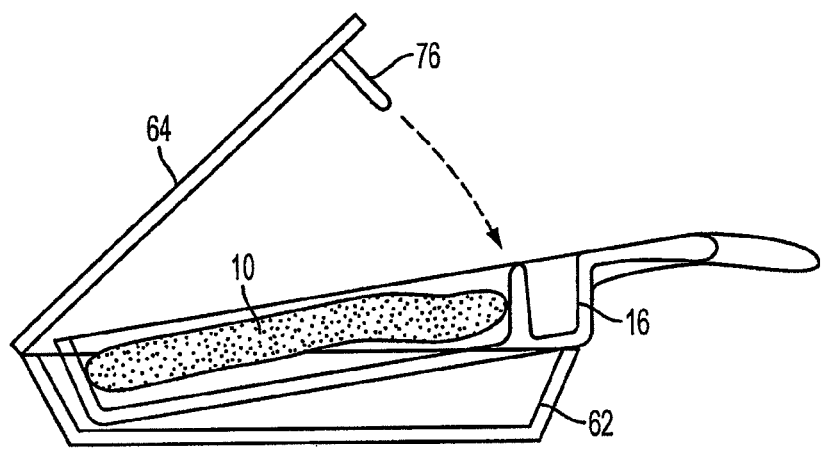

For example, the cutting element could be incorporated into the cassette. FIG. 20A illustrates an example embodiment of a cassette 60 in which the cutting element 76 is incorporated in the cassette lid 64. Thus, as shown in FIG. 20B, as cassette lid 64 is closed, the cutting element 76 is driven through the joining member 16 to separate one or more of the sample containers 10 from the remainder of sample tray 5A, 5B. The cutting element 76 may alternatively be incorporated into the cassette housing 62. Alternatively, a separate cutting lid (not shown) may be configured to snap onto the cassette housing 62 to cut the joining member 16 and then be removed and replaced with the cassette lid 64.

The material used for the cassette 60 is not particularly limited, and may include the same or different materials used to form the tray. In some cases, the cassette 60 is made from the same material as the tray and is manufactured as part of the tray.

Figure 21:
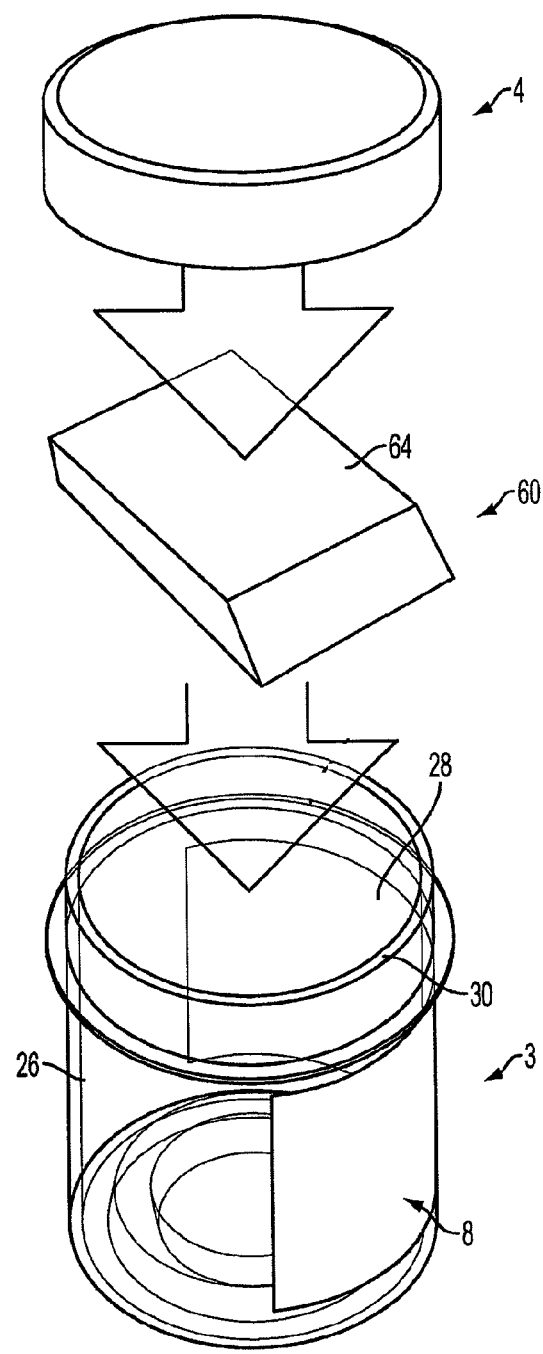
FIG. 21 illustrates insertion of a transport cassette into a transportation apparatus according to a third embodiment of the present application.

The sample cassette 60 may be placed into a shipping transportation container transportation. In FIG. 21, the transportation apparatus includes a lid 4 and a housing 3 and similar in all aspects to the embodiments discussed above.

In FIG. 21, the attachment of the label 8 to one or more of the sample containers 10, the lid 4, the cassette 60 and/or the housing 3 is done during step 1006 of the method of FIG. 14. However, the attachment of the label 8 may occur at any point during the method of FIG. 14 and need not be the last step as shown in FIG. 14.

In FIG. 21, the cassette 60 is inserted in a horizontal orientation, such that the cassette lid 64 of the cassette 60 is substantially parallel to the lid 4. Alternatively, the cassette 60 may be inserted in a vertical orientation, such that the cassette lid 64 of the cassette 60 is substantially parallel to the sidewall 26 of the housing 3.

As noted above, after the cassette 60 is inserted into the transport device 1 a fixing agent chemical is added or released into the transportation container. In order to preserve the one or more collected biopsy tissue samples for subsequent histological analysis, it is necessary to perform a fixation process on the sample (i.e. submerging the sample in a bath of fixation solution).

In this way, the trays can be used to support and orient the biopsy samples throughout the histopathology workflow. Either prior to fixation or after fixation, the samples in the trays can be imaged (by MRI, x-ray, etc.). Thereafter, the trays embedded with wax. Thereafter, the samples (in the trays) can be sectioned with a microtome, and slides can be prepared and stained.

Embodiment 4

Figure 22:
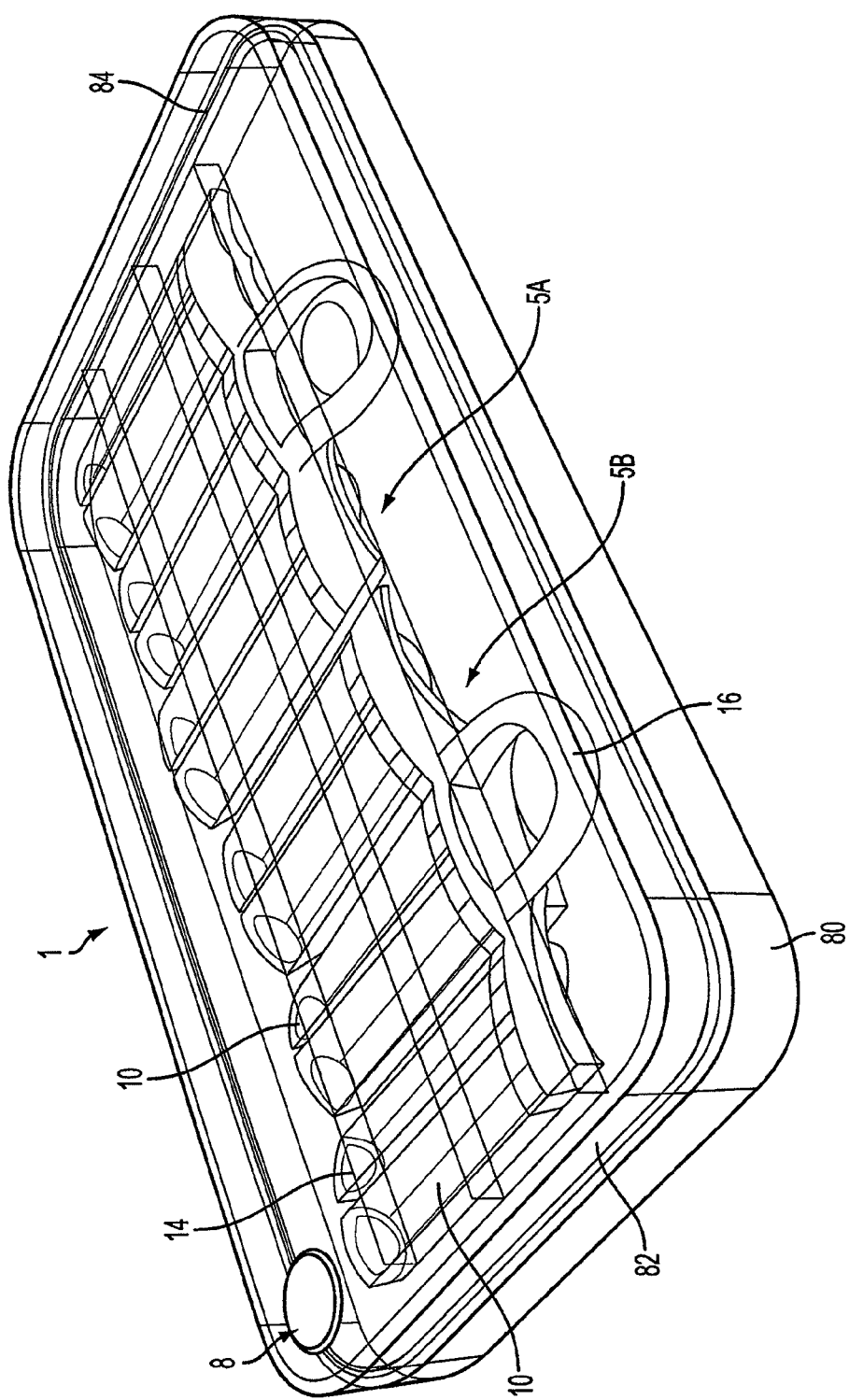
FIG. 22 illustrates insertion of a transport cassette into a transportation apparatus according to a fourth embodiment of the present application.

FIG. 22 illustrates another exemplary embodiment of a biopsy sample transport device 10 according to a fourth exemplary embodiment of the present application. The biopsy sample transport device 10 mirrors the above described embodiments, however in this embodiment, the biopsy sample transport device 10 has a substantially rectangular shape and is formed by a lower housing member 80 and an upper housing member 82. Further, a sealing gasket 84 is disposed at the interface between the lower housing member 80 and the upper housing member 82.

The connection between the lower housing member 80 and the upper housing member 82 is not particularly limited, and may include one or more of a tongue and groove configuration, a snap fitting configuration, a pressure fitting configuration or any other configuration as would be apparent to a person of ordinary skill in the art. Additionally, the sealing gasket 84 is not particularly limited and may be a rubber gasket, a plastic gasket, and O-ring, or any other sealing member as would be apparent to a person of ordinary skill in the. Similar to the embodiments above, the biopsy sample transport device 10 of FIG. 22 is configured to receive one or more sample trays 5A, 5B such that the one or more sample containers 10 are horizontally disposed and aligned in a substantially parallel manner. Such a configuration may permit the orientation of the biopsy core samples disposed within the sample containers to do be maintained during transportation and handling. In this embodiment, similar to the embodiments discussed above, a fixing agent pouch may be provided in the transport device 10. The fixing agent pouch may be provided in the upper housing or lower housing. Alternatively, the lower housing may have two chambers in which the sample trays are in one chamber and the fixing agent pouch is in another chamber.

Embodiment 5

Figure 23A:
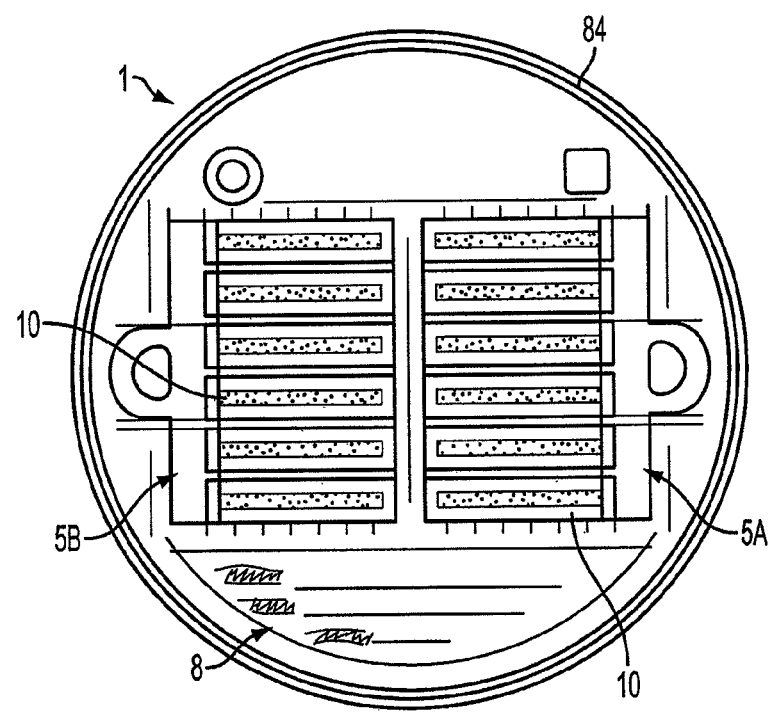
FIGS. 23A-23B illustrate a transport cassette into a transportation apparatus according to a fifth embodiment of the present application.
Figure 23B:
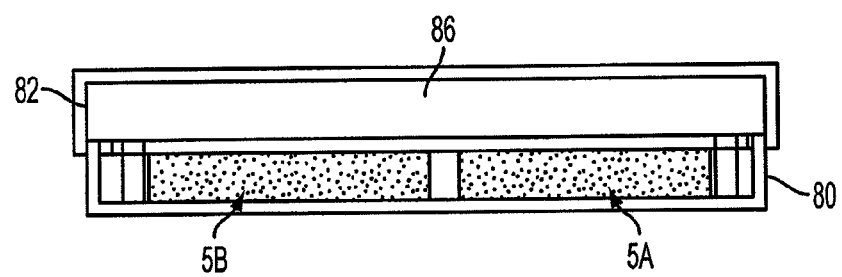

FIG. 23A illustrates a top view of a biopsy sample transport device 10 according to a fifth exemplary embodiment of the present application. FIG. 23B illustrates a side view of the biopsy sample transport device 10 according to the fifth embodiment of the present. This embodiment mirrors the embodiments discussed above, however, in this embodiment, the biopsy sample transport device 10 has a substantially cylindrical shape. Further, in some embodiments, the upper housing member 82 may have a chamber 86 which may enclose a fixing agent pouch for preserving biopsy samples during transport.

Figure 24:
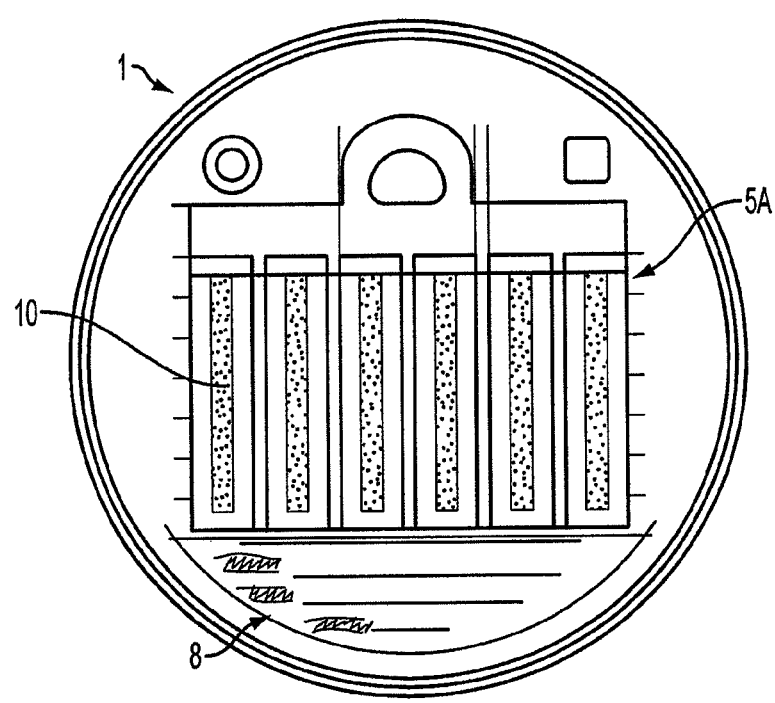
FIG. 24 illustrates a transport cassette into a transportation apparatus according to another exemplary embodiment of the present application.

Alternatively, as shown in FIG. 24, the transport device 10 is sized to hold a single sample tray 5A having a plurality of sample containers 10.

Methods of Processing Biopsy Samples

Figure 25:
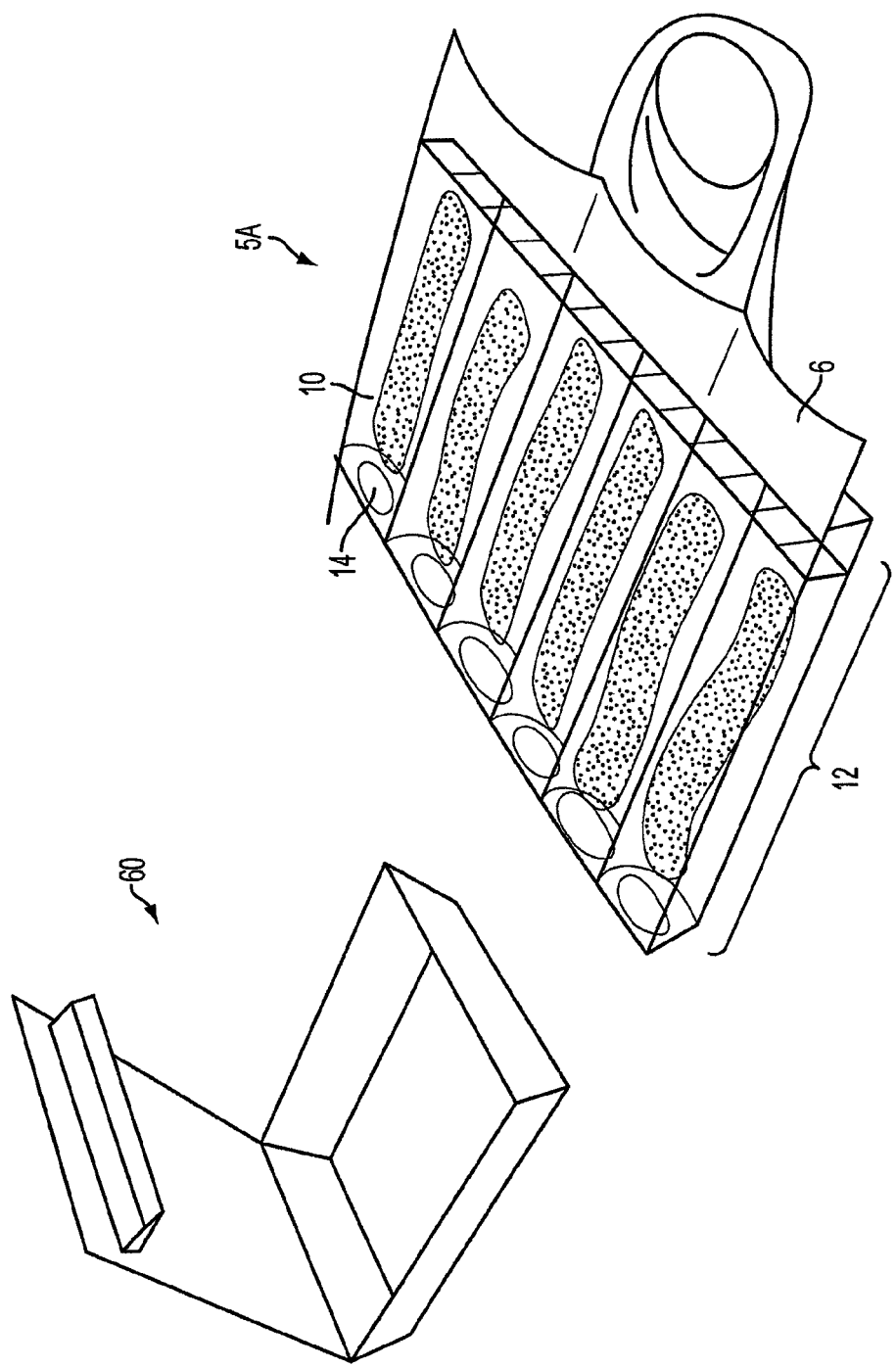
FIG. 25 illustrates a tray next to a tissue cassette according to an example embodiment of the present application.

The sample transport device of the present application is envisioned to allow the biopsy sample to proceed from patient through a histopathology lab with minimum human contact. By way of example, the sample tray 5A will receive the sample from the biopsy device. It can be removed from the device and placed in a container of formalin (either as described herein or via any container). Either prior to fixation or after fixation, the samples in the trays can be imaged (by MRI, x-ray, etc.). Following fixation, the tray can be cut to fit into a standard tissue cassette such as shown in FIG. 25. In FIG. 25, the bracing member 6 of the tray 5A can be cut down and one or more holding structures 12 can be separated from the others and placed into the tissue cassette. Thereafter, the tissue cassette can be processed and thereafter the trays embedded with wax. Thereafter, the samples (in the trays) can be sectioned with a microtome, and slides can be prepared and stained. In this way, the trays can be used to support and orient the biopsy samples throughout the histopathology workflow.

Although a few example embodiments have been shown and described, these example embodiments are provided to convey the subject matter described herein to people who are familiar with this field. It should be understood that the subject matter described herein may be embodied in various forms without being limited to the described example embodiments. The subject matter described herein can be practiced without those specifically defined or described matters or with other or different elements or matters not described. It will be appreciated by those familiar with this field that changes may be made in these example embodiments without departing from the subject matter described herein as defined in the appended claims and their equivalents. Further, any description of structural arrangement of components or relationship there between is merely for explanation purposes and should be used to limit an example embodiment.

Aspects related to the example embodiment have been set forth in part in the description above, and in part should be apparent from the description, or may be learned by practice of embodiments of the application. Aspects of the example embodiment may be realized and attained using the elements and combinations of various elements and aspects particularly pointed out in the following detailed description and the appended claims.

It is to be understood that both the foregoing descriptions are an example and are explanatory only and are not intended to be limiting.

What is claimed is:

1. A biopsy tissue sample transport device comprising:
  a. a tissue storage assembly having at least one sample container comprising a holding structure configured to releasably position a tissue sample, wherein the holding structure comprises a sample access opening formed in a sidewall configured to allow sample insertion or removal therethrough;
  b. a housing containing the tissue storage assembly therein, the housing comprising an assembly insertion opening through which the tissue storage assembly is inserted into the housing;
  c. a sealing member comprising a body and at least one protrusion extending from a surface of the body, the at least one protrusion configured to be inserted into an substantially seal the sample access opening formed in the sidewall of the at least one sample container; and
  d. a lid configured to engage and substantially seal the assembly insertion opening of the housing,
  wherein the sealing member is a structure arranged on an inner wall of the housing and is projected in a first direction, from the inner wall to the assembly insertion opening, so as to engage and seal the sample access opening by abutting the sample access opening, and
  wherein the first direction is parallel to a second direction through which the assembly insertion opening of the housing receives the tissue storage assembly,
  wherein the sealing member comprises an annular shaped member disposed at a bottom of the housing, and the at least one protrusion of the sealing member extending upward from the annular shaped member, and
  wherein the tissue storage assembly is inserted into the housing such that the sample access opening formed in the sidewall of the holding structure of the at least one sample container is oriented downward to engage the at least one protrusion of the sealing member.

2. The biopsy tissue sample transport device according to claim 1, wherein the tissue storage assembly further comprises:
  a cylindrical member comprising a plurality of chambers extending lengthwise through the cylindrical member with one opening provided at one end of each chamber,
  wherein the at least one sample container is configured to be inserted into one of the plurality of chambers extending lengthwise through the cylindrical member.

3. The biopsy tissue sample transport device according to claim 1, wherein the at least one sample container is sized and shaped to receive a core biopsy sample.

4. The biopsy tissue sample transport device according to claim 1,
  a. further comprising:
    i. a fixing agent pouch disposed within at least one of the lid and the housing, the fixing agent pouch comprising:
      1. a casing having a frangible portion;
      2. a fixing agent chemical selected to fix and preserve the tissue samples for later analysis.

5. The biopsy tissue sample transport device according to claim 4,
  a. wherein the fixing agent pouch is disposed within the lid of the biopsy tissue sample transport device;
  b. wherein the lid further comprises a breaking member; and
  c. wherein the breaking member is configured to engage the frangible portion of the casing of the fixing agent pouch upon sealing of the lid and rupture the frangible portion of the casing causing the fixing agent chemical to be released into the housing.

6. The biopsy tissue sample transport device according to claim 4, a. wherein the fixing agent pouch is disposed within the housing of the biopsy tissue sample transport device; and b. wherein the biopsy tissue sample transport device further comprises a breaking member disposed within the housing and configured to engage the frangible portion of the casing of the fixing agent pouch upon at least one of insertion of the tissue storage assembly or sealing of the lid and rupture the frangible portion of the casing causing the fixing agent chemical to be released into the housing.

7. The biopsy tissue sample transport device according to claim 4, a. wherein the fixing agent pouch is further disposed within a central cylindrical hollow region of the housing; and b. wherein the biopsy tissue sample transport device further comprises:

i. a breaking member, which is disposed within the housing and which is configured to engage the frangible portion of the casing of the fixing agent pouch upon at least one of insertion of the tissue storage assembly or sealing of the lid, and rupture the frangible casing causing the fixing agent chemical to be released into the housing; and ii. a plunger member configured to push the fixing agent out of the central cylindrical hollow region of the housing and into at least one longitudinal extending slots of the housing in response to sealing of the lid to the housing.

8. The biopsy tissue sample transport device according to claim 7, a. wherein at least one of the housing and a lid comprises a post member configured to engage the plunger member and provide a squeezing force to push the fixing agent out of the central cylindrical hollow region in response to sealing of the lid to the housing.

9. The biopsy tissue sample transport device according to claim 1, further comprising an ID tag attached to at least one of the housing, the lid, and the tissue storage assembly.

10. The biopsy tissue sample transport device according to claim 9, wherein the ID tag attached to at least one of the housing, the lid, and the tissue storage assembly comprises a computer readable ID tag.

11. The biopsy tissue sample transport device according to claim 10, wherein the computer readable ID tag comprises at least one of a readable writable RFID tag, a one-dimensional barcode, a two-dimensional barcode and a three-dimensional barcode.

12. The biopsy tissue sample transport device according to claim 10, wherein the computer readable ID tag contains information unique to the tissue sample.

13. The biopsy tissue sample transport device according to claim 12, wherein the information unique to the tissue sample includes one or more of patient identification information, sample collection site location information, collection temperature, collection time, and collection conditions.

14. The biopsy tissue sample transport device according to claim 1, wherein the sample access opening is further configured to allow insertion and removal of the sample container therethrough along a first direction, the assembly insertion opening is further configured to receive an insertion of the tissue storage assembly and the holding structure thereof into the housing along a second direction, and during the insertion, the first direction is substantially equal to the second direction.

15. The biopsy tissue sample transport device according to claim 1, wherein when the lid is secured to the housing an interior of the housing is fully sealed from an exterior of the housing.

16. The biopsy tissue sample transport device according to claim 1, wherein the sealing member protrudes from the interior of the housing and to the access opening.

17. The biopsy tissue sample transport device according to claim 1, wherein the sealing member is directly attached to the housing.

18. The biopsy tissue sample transport device according to claim 1, wherein the tissue storage assembly further comprises a plurality of holding structures each with one of a plurality of sample access openings, wherein the plurality of holding structures are connected by a flexible material such that the tissue storage assembly is folded into a shape of an inner circumference of the housing, and wherein the plurality of holding structures is longitudinally arranged in line with a longitudinal direction of the housing.

* * * * *